US012765769B2

(12) United States Patent
Yao et al.

(10) Patent No.: US 12,765,769 B2
(45) Date of Patent: Oct. 20, 2026

(54) EYE TRACKING APPARATUS AND EYE TRACKING METHOD

(71) Applicant: Huawei Technologies Co., Ltd., Shenzhen (CN)

(72) Inventors: Sicheng Yao, Dongguan (CN); Zhaoxue Wang, Shenzhen (CN); He Wang, Dongguan (CN)

(73) Assignee: HUAWEI TECHNOLOGIES CO., LTD., Shenzhen (CN)

(*) Notice: Subject to any disclaimer, the term of this patent is extended or adjusted under 35 U.S.C. 154(b) by 245 days.

(21) Appl. No.: 18/748,301

(22) Filed: Jun. 20, 2024

(65) Prior Publication Data

US 2024/0341593 A1 Oct. 17, 2024

Related U.S. Application Data

(63) Continuation of application No. PCT/CN2022/139614, filed on Dec. 16, 2022.

(30) Foreign Application Priority Data

Dec. 20, 2021 (CN) ........................ 202111567442.0

(51) Int. Cl.
*A61B 3/113* (2006.01)

(52) U.S. Cl.
CPC .................................... *A61B 3/113* (2013.01)

(58) Field of Classification Search
CPC .... A61B 3/113; G02B 27/0093; G06V 40/19; G06F 3/013
USPC .......................................................... 351/209
See application file for complete search history.

(56) References Cited

U.S. PATENT DOCUMENTS

| | | | | | |
|---|---|---|---|---|---|
| 6,299,307 | B1 * | 10/2001 | Oltean | A61B 3/113 | 606/5 |
| 2004/0170304 | A1 * | 9/2004 | Haven | G06V 40/19 | 382/115 |
| 2010/0103375 | A1 * | 4/2010 | Chao | A61B 3/113 | 351/210 |
| 2010/0220291 | A1 * | 9/2010 | Horning | G06V 40/19 | 351/210 |
| 2015/0346815 | A1 * | 12/2015 | Horesh | G06F 3/043 | 345/173 |
| 2019/0235248 | A1 * | 8/2019 | Ollila | G02B 27/0093 | |
| 2021/0271317 | A1 * | 9/2021 | Sharma | G06T 7/0016 | |
| 2023/0195220 | A1 * | 6/2023 | Boyle | G02B 27/0093 | 348/78 |

(Continued)

FOREIGN PATENT DOCUMENTS

CN 108646910 A 10/2018

*Primary Examiner* — Bumsuk Won
*Assistant Examiner* — Seth D Moser
(74) *Attorney, Agent, or Firm* — Conley Rose, P.C.

(57) ABSTRACT

An eye tracking apparatus includes M light sources configured to emit N different types of light to an eye of a user, where M is a positive integer greater than or equal to 2, and N is a positive integer greater than or equal to 2, and includes a camera, where the camera includes a light filtering component and an image sensor. The light filtering component is configured to filter reflected light that is reflected after the M light sources irradiate the eye, includes a plurality of light filtering units, includes at least N sub-regions, and filters at least the N different types of light, where one sub-region filters one type of light.

20 Claims, 12 Drawing Sheets

(a) (b)

(56) References Cited

U.S. PATENT DOCUMENTS

2024/0350004 A1 * 10/2024 Bai ......................... G06F 3/013

* cited by examiner (a)

(b)

EYE TRACKING APPARATUS AND EYE TRACKING METHOD

CROSS-REFERENCE TO RELATED APPLICATIONS

This is a continuation of International Patent Application No. PCT/CN2022/139614 filed on Dec. 16, 2022, which claims priority to Chinese Patent Application No. 202111567442.0 filed on Dec. 20, 2021. The disclosures of the aforementioned applications are hereby incorporated by reference in their entireties.

TECHNICAL FIELD

This disclosure relates to the fields of terminals and communication technologies, and in particular, to an eye tracking apparatus and an eye tracking method

BACKGROUND

An electronic device can use actions of a user as inputs, to perform different operations or functions. For example, the electronic device may perform an operation, for example, an operation of opening an application, in response to a touch gesture of the user. For another example, an eye movement may be tracked and detected (namely, eye tracking), so that the electronic device may perform different operations or functions in response to an eye tracking result. In a head mounted device, eye tracking may be used to perform an operation, for example, a scrolling operation or an operation of opening an application. In addition, eye tracking may be further applied to a function of enhancing display effect. For example, when the head mounted device performs display, eye tracking is applied to fixation point (namely, a position at which a human eye is watching) rendering, that is, rendering of a high-quality image in a focus region (namely, a region in which a fixation point is located) of a vision field of the user, so that better visual effect can be achieved for the user.

A method mainly used for eye tracking is a pupil-iris reflection method. To be specific, a light source emits light in front of a human eye, and when light of the light source is irradiated to the human eye, reflection occurs in a region, for example, a pupil or an iris of the human eye. In this way, a camera in front of the human eye may obtain reflected light and a human eye image. An image formed by the reflected light on the camera is a light spot. Based on the light spot and the human eye image, a fixation direction of a person may be obtained, so that a fixation point of the human eye may be obtained. How to accurately determine a fixation point of a human eye is a problem to be resolved.

SUMMARY

This disclosure provides an eye tracking apparatus and an eye tracking method, to accurately match a light source with a light spot, so as to accurately determine a fixation point of a human eye.

According to a first aspect, an embodiment of this disclosure provides an eye tracking apparatus, and the eye tracking apparatus includes M light sources configured to emit N different types of light to an eye of a user, where one light source emits one type of light, M is a positive integer greater than or equal to 2, N is a positive integer greater than or equal to 2, and N is less than or equal to M. The eye tracking apparatus includes a camera module, where the camera module includes a light filtering component and an image sensor, where the light filtering component is configured to filter at least a part of light reflected after the M light sources irradiate the eye, the light filtering component includes a plurality of light filtering units, the light filtering unit includes at least N different types of sub-regions, and the different types of sub-regions filter different types of light. The image sensor is configured to obtain the at least a part of light that passes through the light filtering component, to obtain a human eye light spot image, where the at least a part of light that passes through the light filtering component forms at least one light spot on the human eye light spot image.

In the foregoing embodiment, because each light source emits light of a corresponding type (for example, a wavelength), and each sub-region may transmit light of a corresponding type, when light of a light source is reflected by a human eye and reaches the light filtering component, if the light of the light source matches a sub-region, the light of the light source may pass through the sub-region, and a light spot is formed in the image sensor. Therefore, one or more types of light that form the light spot in the human eye light spot image can be reflected by the light spot, which helps improve accuracy and efficiency of matching a light spot with a light source, and improves accuracy of a human eye fixation point determined by eye tracking.

In some possible implementations, the image sensor includes an array of pixels, there is a correspondence between the sub-region and the pixel, one light spot includes a plurality of pixels, and one light spot corresponds to the N different types of sub-regions. There is a correspondence between the sub-region and the pixel, so that it can be ensured that whether there is corresponding light passing through each sub-region can be reflected by the human eye light spot image, and a type of light that forms the light spot can be more accurately determined, which helps improve accuracy of eye tracking.

For example, when one or more of the following conditions are met, it can be better ensured that whether there is corresponding light passing through each sub-region can be reflected by the human eye light spot image: an area of the sub-region is less than or equal to five pixels of the image sensor, the area of the sub-region is less than or equal to 1/N of an area of one light spot, or the sub-regions are in a one-to-one correspondence with the pixels of the image sensor.

In some embodiments, M is greater than or equal to 4, and/or Nis greater than or equal to 4. When M and N are greater than or equal to 4, there are a large quantity of light sources and a large quantity of light types, which is more conducive to distinguishing between different light sources, so that a light source can be more accurately matched with a light spot.

In some embodiments, N is less than M, and at least two of the light sources emit light of a same type, so that requirements on a type of the light source and a type of a filter can be reduced. The two light sources that emit light of the same type are not adjacent, which can effectively avoid impact between adjacent light sources. For example, the M light sources include a plurality of light source groups, each light source group includes at least two light sources that emit light of a same type, and light sources in different light source groups emit light of different types. In this way, it can be ensured that the light source is effectively identified and matched, and requirements on components such as the light source and the filter can be reduced.

In some embodiments, the two light sources that emit light of the same type have different light emitting frequencies or different light emitting time, and the light sources that emit light of the same type may be further distinguished. In this way, it can be ensured that the light source is effectively identified and matched, and requirements on components such as the light source and the filter can be reduced.

According to a second aspect, an embodiment of this disclosure provides an eye tracking method, where the method includes emitting N different types of light to an eye of a user by using M light sources, where M is a positive integer greater than or equal to 2, N is a positive integer greater than or equal to 2, and N is less than or equal to M. The method includes filtering, by a light filtering component in a camera module, at least a part of light reflected after the M light sources irradiate the eye, where the light filtering component includes a plurality of light filtering units, the light filtering unit includes at least N different types of sub-regions, and the different types of sub-regions filter different types of light. The method includes obtaining, by an image sensor in the camera module, the at least a part of light that passes through the light filtering component, to obtain a human eye light spot image, where the at least a part of light that passes through the light filtering component forms at least one light spot on the human eye light spot image.

In the foregoing embodiment, because each light source emits light of a corresponding type (for example, a wavelength), and each sub-region may transmit light of a corresponding type, when light of a light source reaches the light filtering component, if the light of the light source matches a sub-region, the light of the light source may pass through the sub-region, and a light spot is formed in the image sensor. Therefore, one or more types of light that form the light spot in the human eye light spot image can be reflected by the light spot, which helps improve accuracy and efficiency of matching a light spot with a light source, and improves accuracy of a human eye fixation point determined by eye tracking.

In some possible implementations, there is a correspondence between the sub-region and a pixel of the image sensor, one light spot includes a plurality of pixels, and one light spot corresponds to N different types of sub-regions. There is a correspondence between the sub-region and the pixel, so that it can be ensured that whether there is corresponding light passing through each sub-region can be reflected by the human eye light spot image, and a type of light that forms the light spot can be more accurately determined, which helps improve accuracy of eye tracking.

For example, when one or more of the following conditions are met, it can be better ensured that whether there is corresponding light passing through each sub-region can be reflected by the human eye light spot image: an area of the sub-region is less than or equal to five pixels of the image sensor, the area of the sub-region is less than or equal to 1/N of an area of one light spot, or the sub-region is in a one-to-one correspondence with the pixels of the image sensor.

In some embodiments, M is greater than or equal to 4, and/or N is greater than or equal to 4. When M and N are greater than or equal to 4, there are a large quantity of light sources and a large quantity of light types, which is more conducive to distinguishing between different light sources, so that a light source can be more accurately matched with a light spot.

In some embodiments, N is less than M, and at least two of the light sources emit light of a same type, so that requirements on a type of the light source and a type of a filter can be reduced. The two light sources that emit light of the same type are not adjacent, which can effectively avoid impact between adjacent light sources. For example, the M light sources include a plurality of light source groups, each light source group includes at least two light sources that emit light of a same type, and light sources in different light source groups emit light of different types. In this way, it can be ensured that the light source is effectively identified and matched, and requirements on components such as the light source and the filter can be reduced.

In some embodiments, the two light sources that emit light of the same type have different light emitting frequencies or different light emitting time, and the light sources that emit light of the same type may be further distinguished. In this way, it can be ensured that the light source is effectively identified and matched, and requirements on components such as the light source and the filter can be reduced.

According to a third aspect, an embodiment of this disclosure further provides an electronic device, where the electronic device includes one or more processors, M light sources, a light filtering component, an image sensor, a memory, and one or more programs, the one or more programs are stored in the memory and are configured to be executed by the one or more processors, the one or more programs include instructions, and the instructions are used to obtain a fixation direction of a human eye based on a human eye light spot image.

According to a fourth aspect, an embodiment of this disclosure further provides a computer-readable storage medium, where the computer-readable storage medium stores instructions, and when the instructions are run on a computer, a fixation direction of a human eye is obtained based on a human eye light spot image.

According to a fifth aspect, an embodiment of this disclosure further provides a computer program product including instructions, and when the computer program product runs on a computer, a fixation direction of a human eye is obtained based on a human eye light spot image.

DESCRIPTION OF EMBODIMENTS

Figure 1:
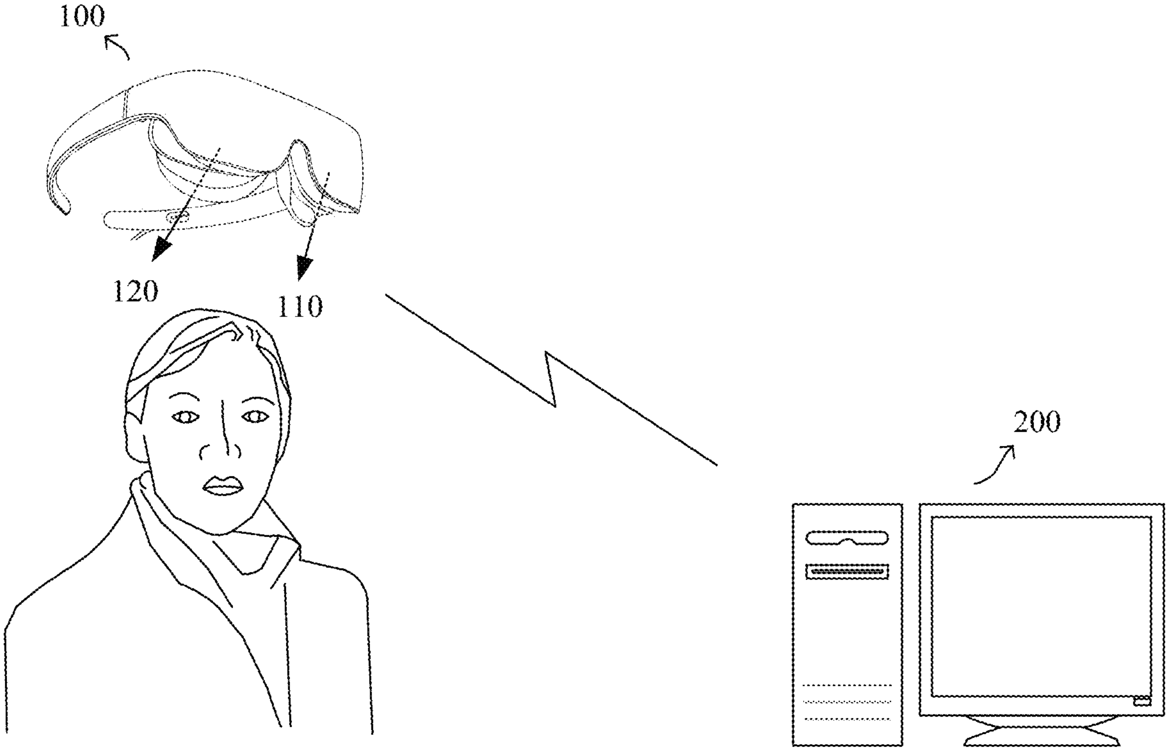
FIG. 1 is a schematic diagram of a virtual reality (VR) system according to an embodiment of this disclosure.

The following describes some terms in embodiments of this disclosure, to facilitate understanding of persons skilled in the art.

In embodiments of this disclosure, "at least one" means one or more, and "a plurality of" means two or more. In addition, it should be understood that in descriptions of this disclosure, words such as "first" and "second" are merely intended for purposes of description, and should not be understood as expressing or implying relative importance or a sequence. For example, a first region and a second region do not represent importance degrees of the two, or represent a sequence of the two, and are merely used to distinguish between regions. The term "and/or" in embodiments of this disclosure describes only an association relationship for describing associated objects and represents that three relationships may exist. For example, A and/or B may represent the following three cases: Only A exists, both A and B exist, and only B exists. In addition, the character "/" in this specification generally indicates an "or" relationship between the associated objects.

A VR technology is a human-computer interaction method created by using computer and sensor technologies. The VR technology integrates a computer graphics technology, a computer simulation technology, a sensor technology, a display technology, and the like, and can create a virtual environment. The virtual environment includes a three-dimensional stereoscopic realistic image generated and dynamically played in real time by a computer, to bring visual perception to a user. In addition, in addition to visual perception generated by a computer graphics technology, there is perception including an auditory sense, a tactile sense, a force sense, and a motion, and even a sense of smell and a sense of taste, which is also referred to as multi-perception. In addition, a head rotation, an eye, a gesture, or another human body behavior action of the user may be further detected, and the computer processes data corresponding to the action of the user, responds to the action of the user in real time, and feeds back the action to five sense organs of the user, to generate the virtual environment. For example, the user may see a VR game interface by wearing a VR wearable device, and may interact with the VR game interface by using an operation, for example, a gesture or a handle, as if the user is in a game.

An augmented reality (AR) technology is to superimpose a virtual object generated by a computer on a real-world scene, to enhance the real world. That is, in the AR technology, a real-world scenario is collected, and then a virtual environment is added to the real world.

Therefore, a difference between the VR technology and the AR technology lies in that the VR technology creates a complete virtual environment, and all objects seen by a user are virtual objects, while the AR technology superimposes a virtual object in a real world, that is, includes both an object in the real world and the virtual object. For example, the user wears transparent glasses, and can see a real environment around the user by using the glasses, and a virtual object may be further displayed on the glasses. In this way, the user can see both a real object and a virtual object.

A mixed reality technology (MR) introduces real-world scenario information (or referred to as real scenario information) into a virtual environment, and establishes a bridge between the virtual environment, the real world, and a user for interactive feedback information, thereby enhancing a sense of reality of user experience. Specifically, a real object is virtualized (for example, a camera is used to scan the real object for three-dimensional reconstruction to generate a virtual object), and a virtualized real object is introduced into a virtual environment. In this way, the user can see the real object in the virtual environment.

It should be noted that technical solutions provided in embodiments of this disclosure may be applied to a scenario in which an electronic device used for eye tracking is a head mounted device, for example, a VR scenario, an AR scenario, or an MR scenario, or may be applied to another scenario in which an electronic device used for eye tracking is a non-head mounted device, for example, a scenario in which a large-screen device, for example, a terminal device (for example, a mobile phone, a tablet computer, and the like), a computer monitor, an intelligent vehicle, or a television is used for eye tracking. In addition, in an intelligent vehicle driving scenario, a fixation point of a human eye can be more accurately determined by using the technical solutions provided in embodiments of this disclosure, and eye tracking may be performed more quickly and accurately. In conclusion, this method is applicable to any scenario in which a fixation point of a human eye is accurately determined for eye tracking.

For ease of understanding, the following mainly uses a VR scenario as an example for description.

For example, FIG. 1 is a schematic diagram of a VR system according to an embodiment of this disclosure. The VR system includes a VR wearable device (a VR head mounted display device 100 is used as an example in this embodiment of this disclosure) and an image processing device 200. The VR system may be referred to as a VR split-type machine. The VR head mounted display device 100 may be connected to the processing device 200. A connection between the VR head mounted display device 100 and the processing device 200 includes a wired or wireless connection. The wireless connection may be BLUETOOTH (BT), BLUETOOTH Low Energy (BLE), a wireless local area network (WLAN) (for example, a wireless fidelity (Wi-Fi) network), ZIGBEE, frequency modulation (FM), a near field wireless communication technology (NFC), an infrared technology (IR), a universal 2.4G/5G frequency band wireless communication connection, or the like.

In some embodiments, the image processing device 200 may perform processing calculation. For example, the image processing device 200 may generate an image and process the image (a processing manner is described below), and then send the processed image to the VR head mounted display device for display. The image processing device 200 may include a host (for example, a VR host) or a server (for example, a VR server). The VR host or the VR server may be a device having a large computing capability. For example, the VR host may be a device such as a mobile phone, a tablet computer, or a notebook computer, and the VR server may be a cloud server or the like.

In some embodiments, the VR head mounted display device 100 may be glasses, a helmet, or the like. Two display devices are usually disposed on the VR head mounted display device 100, namely, a display device 110 and a display device 120. The display device of the VR head mounted display device 100 can display an image to a human eye. In the embodiment shown in FIG. 1, the display device 110 and the display device 120 are wrapped inside the VR glasses. Therefore, arrows used to indicate the display device 110 and the display device 120 in FIG. 1 are represented by dashed lines.

In some embodiments, the VR head mounted display device 100 further has functions including image generation and processing and the like, that is, the VR head mounted display device 100 does not use the image processing device 200 in FIG. 1. Such a VR head mounted display device 100 may be referred to as an all-in-one VR machine.

Figure 2A:
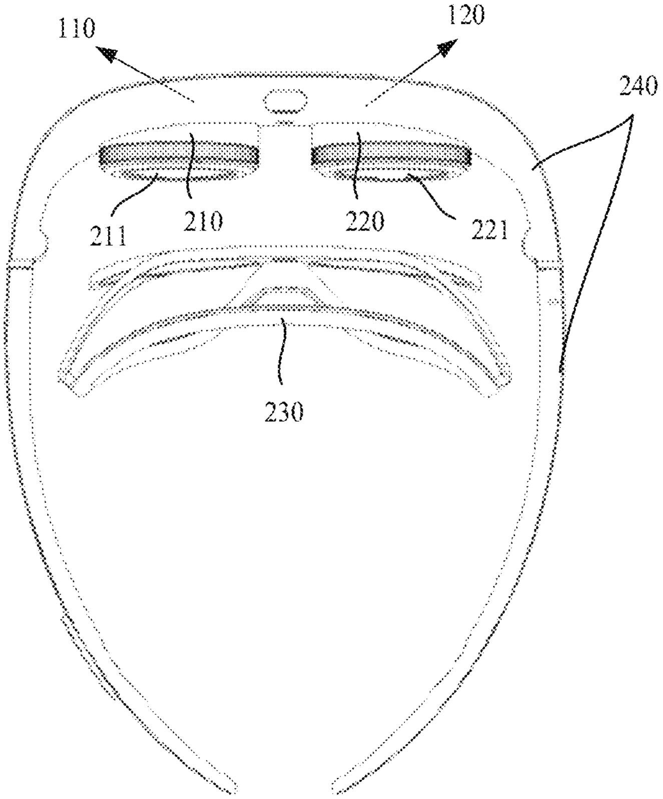
FIG. 2A is a schematic diagram of a VR head mounted display device according to an embodiment of this disclosure.
Figure 2A:
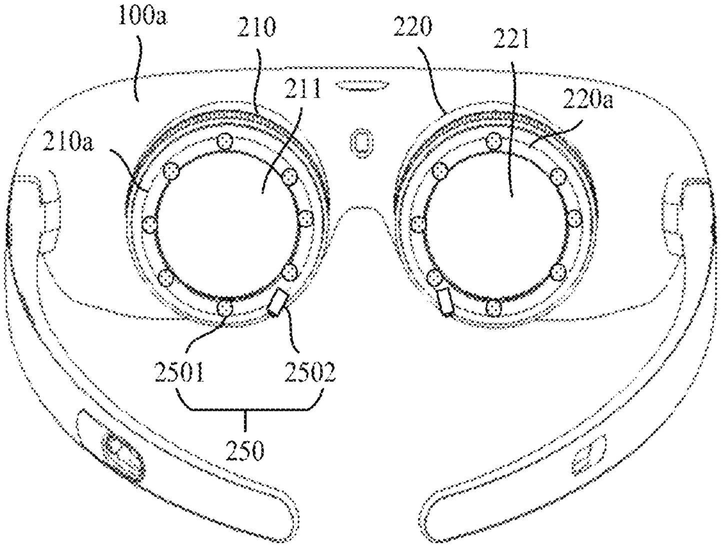

FIG. 2A is a schematic diagram of the VR head mounted display device 100. As shown in (a) in FIG. 2A, the VR head mounted display device 100 includes an optical display module 210 and an optical display module 220. The optical display module 210 includes a display device and an optical device 211. The optical display module 220 includes a display and an optical device 221. In some embodiments, the optical display module 210 and the optical display module 220 further include an optical device. In some embodiments, the optical display module 210 and the optical display module 220 each may be lens tubes. The lens tube is hollow cylindrical. In other words, the optical device is accommodated in the lens tube, and the optical device and the display device are disposed on the VR head mounted display device 100 by using the lens tube. When a user wears the VR head mounted display device 100, the optical display module 210 may be configured to display an image to a left eye of the user. The optical display module 220 may be configured to display an image to a right eye of the user. It may be understood that the VR head mounted display device 100 shown in (a) in FIG. 2A may further include other components, for example, further include a support part 230 and a support 240. The support part 230 is configured to support the VR head mounted display device 100 on a nose beam, and the support 240 is configured to support the VR head mounted display device 100 on both ears, to ensure that the VR head mounted display device 100 is stably worn. As shown in (b) in FIG. 2A, at least one eye tracking module (including M light sources 2501 and at least one camera module 2502) may be disposed on the VR head mounted display device 100, and is configured to track a movement of a human eye, to determine a fixation point of the human eye. In some embodiments, a light source 2501 may be disposed on an end surface 100*a* that is of the VR head mounted display device 100 and that faces a face (or an eye of the user). In addition, a camera module 2502 may be further disposed on the end surface 100*a* that is of the VR head mounted display device 100 and that faces the face (or the eye of the user). For example, the light source 2501 is located on an end surface 210*a* that is of the lens tube and that faces the eye, and the end surface 210*a* that is of the lens tube and that faces the eye may be understood as a part of the end surface 100*a*. An eye tracking module 250 on the optical display module 210 is used as an example. In some embodiments, the eye tracking module 250 includes a light source 2501 and a camera module 2502. For example, eight light sources 2501 are disposed on the end surface 210*a* that is of the lens tube and that faces the eye, the eight light sources 2501 may be evenly distributed in a circular shape, and the camera module 2502 may be disposed on the end surface 210*a* that is of the lens tube and that faces the eye. The light sources 2501 and the camera module 2502 may be disposed around a side that is of the optical device 211 and that faces the eye.

Figure 2B:
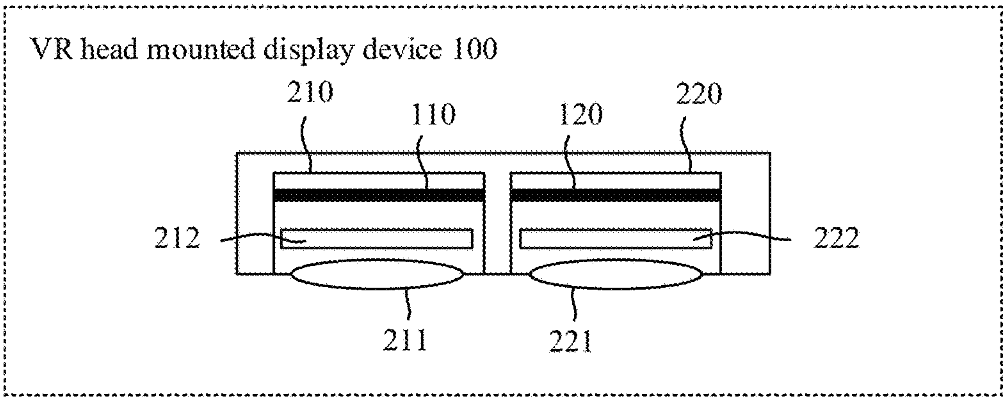
FIG. 2B is a simplified schematic diagram of a VR head mounted display device according to an embodiment of this disclosure.

For ease of description, FIG. 2B may be understood as a simplified VR head mounted display device 100 in FIG. 2A. For example, FIG. 2B shows only the optical display module 210 and the optical display module 220, and other components are not shown. As shown in FIG. 2B, when the user wears the VR head mounted display device 100, the display device 110 is located on a side that is of the optical device 211 and that faces away from the left eye, the display device 120 is located on a side that is of the optical device 221 and that faces away from the right eye, and the optical device 211 and the optical device 221 are symmetrical relative to a center line of a face or a center line D of the VR head mounted display device 100. The center line of the face may be a perpendicular line between the right eye and the right eye. The center line D of the VR head mounted display device 100 may be a center line of the end surface 100*a*, a center line of support 240, or the like. When the display device 110 displays an image, light emitted by the display device 110 is converged to a left eye of a person through the optical device 211. When the display device 120 displays an image, light emitted by the display device 120 is converged to a right eye of the person through the optical device 221. In some embodiments, the VR head mounted display device 100 may further include an optical device 212 and an optical device 222. The optical device 212 and the optical device 211 form a lens group, and the optical device 222 and the optical device 221 form a lens group. The lens group may include at least one optical device. One or more optical devices in the lens group may be adjusted to change a focal length of the lens group. For example, positions of the one or more optical devices in the lens group may move away from or close to the display device, to change the focal length.

It should be noted that composition of the VR head mounted display device 100 shown in FIG. 2A or FIG. 2B is merely a logical schematic diagram. In specific implementation, a quantity of optical devices and/or display devices may be flexibly set based on different requirements. For example, in some embodiments, the display device 110 and the display device 120 may be two independent display devices, or may be two display regions on a same display device. In some embodiments, the display device 110 and the display device 120 may each be a display, for example, a liquid crystal display, a light-emitting diode (LED) display, or another type of display device. This is not limited in this embodiment of this disclosure. In some other embodiments, the optical device 212 and the optical device 211 may be two independent optical devices, or may be different parts on a same optical device. In some embodiments, the optical device 212 and the optical device 211 may be one or more optical devices of a reflection mirror, a transmitting mirror, an optical waveguide, or the like, or may increase an angle of view. For example, the optical device 212 and the optical device 211 may be a lens group formed by a plurality of transmitting mirrors. For example, the optical device may be a Fresnel lens and/or an aspheric lens. This is not limited in this embodiment of this disclosure.

Figure 3:
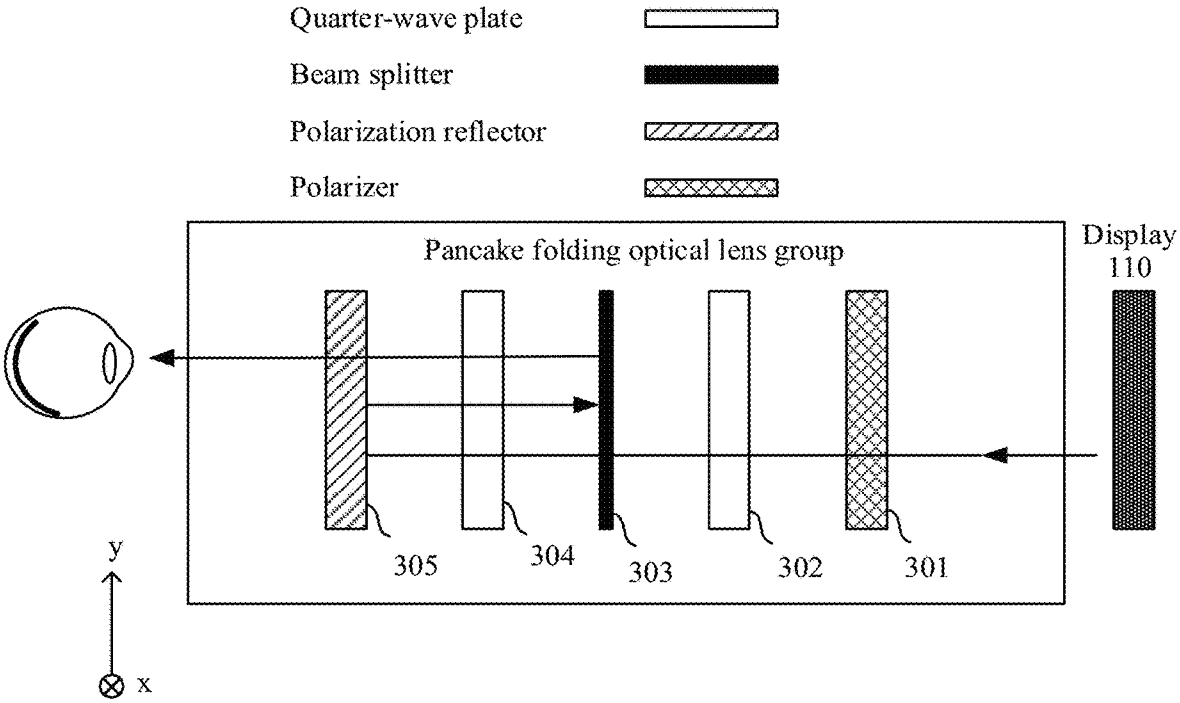
FIG. 3 shows an example of an optical display module according to an embodiment of this disclosure.

FIG. 3 shows an example of the optical display module 210. The display device 110 in the optical display module 210 is a display 110. The optical display module 210 includes five optical devices (for example, 301 to 305), and a lens group including a pancake folding optical lens group (pancake lens group for short below) including the five optical devices (for example, 301 to 305). The following describes a structure of the pancake lens group and a light processing mechanism of the pancake lens group when the pancake lens group works by using an example in which light is emitted from the display 110 of the optical display module 210 and is emitted into a human eye.

As shown in FIG. 3, the pancake lens group may include at least five optical devices (for example, 301 to 305). A specific implementation of any optical device in 301 to 305 may be an optical lens having a corresponding function, or a function corresponding to the component is implemented by using an optical coating on an adjacent lens or another optical component.

In this example, 301 may be a polarizer (P). 302 may be a quarter-wave plate (QWP). 303 may be implemented by using a partial-transmission partial-reflection beam splitter (BS). 304 may be a quarter-wave plate. 305 may be implemented by using a polarization reflector (PR).

As shown in FIG. 3, after incident light is incident to 301, the incident light may be sequentially transmitted in an order of 302, 303, 304, and 305.

For example, the light may be modulated into linearly polarized light (that is, planar polarized light) after passing through 301. In some embodiments, a modulation direction of 301 may be set to a y-axis direction. In this way, after 301, the incident light may be modulated into linearly polarized light in the y-axis direction. Then, the linearly polarized light may be adjusted to rotationally polarized light by 302. For example, if a fast axis direction of 302 and the y axis are at an angle of 45°, the linearly polarized light may be adjusted to right-handed polarized light after passing through 302. A wave plate has a fast axis and a slow axis, the fast axis and the slow axis are perpendicular to each other, and the polarized light has a slightly higher speed in a fast axis direction. The right-handed polarized light may be incident to 303. Because of a semi-transmission semi-reflection characteristic of 303, a part of the right-handed polarized light may be transmitted through 303, and the other part of the light is reflected by 303. The right-handed polarized light transmitted through 303 may be incident to 304. When a fast axis direction of 304 is the same as that of 302, the right-handed polarized light that is transmitted through 303 may directly penetrate 304 and be incident into 305. The right-handed polarized light incident into 305 may be modulated into linearly polarized light in an x-axis direction, and is reflected on a surface of 305.

The light reflected by 305 may pass through 304 to 303 and be reflected in 303.

For example, light reflected on the surface 305 may pass through 304 and be modulated into right-hand polarized light, and a part of the right-hand polarized light may be reflected on a surface of 303. It should be noted that after being reflected on the surface of 303, the right-hand polarized light may be modulated into left-hand polarized light.

The left-hand polarized light reflected by 303 may be emitted out of the pancake lens group through 304 to 305, and finally be incident into a human eye.

For example, after 304, the left-hand polarized light may be modulated into linearly polarized light (that is, planar polarized light) whose polarization direction is in the y-axis direction. Then, the linearly polarized light in the y-axis direction may be emitted out of the pancake lens group through 305, and be incident into the human eye. It may be understood that, in some embodiments, a polarization transmission characteristic of 305 may be set to transmission of linearly polarized light in the y-axis direction. In this way, it can be ensured that the linearly polarized light in the y-axis direction can be smoothly emitted from 305.

In this way, the light may be transmitted in a folding manner in the pancake lens group in an order of 301, 302, 303, 304, 305, 304, 303, 304, and 305, thereby achieving effect of folding an optical path. Therefore, light transmission of a long optical path can be implemented in small space (for example, inside the optical display module 210 of the VR wearable device).

In the example shown in (b) in FIG. 2A, the camera module 2502 may be located on an end surface that is of the optical display module 210 and that is close to a face, and may be located between any two light sources 2501. For example, the camera module 2502 may be located between two light sources 2501 in a lower right corner. In this way, light reflected when the light source 2501 irradiates the eye is not refracted by the lens group, and may be directly received by the camera module 2502, so that eye tracking calculation can be more accurate.

In some embodiments, the camera module 2502 may be located on a side that is of one of the optical devices and that faces away from the human eye, so that the camera module 2502 may be far away from the eye of the user, to receive more light reflected by the eye, thereby obtaining more light spot information, and improving detection precision. For example, in FIG. 3, the camera module 2502 may be located between 303 and 302, or between two other adjacent optical devices. It may be understood that although the camera module 2502 is located between the optical devices, the camera module 2502 is located outside a transmission range of the optical path, to avoid blocking light of the display. In some embodiments, the camera module 2502 may be located between the lens group and the display 110. It may be understood that although the camera module 2502 is located between the lens group and the display 110, the camera module 2502 is located outside a transmission range of the optical path, to avoid blocking light of the display. In this way, the camera module 2502 may be placed based on a position at which light reflected when the light source irradiates the eye can be better received, so that a focus obtained through eye tracking is more accurate.

Figure 4:
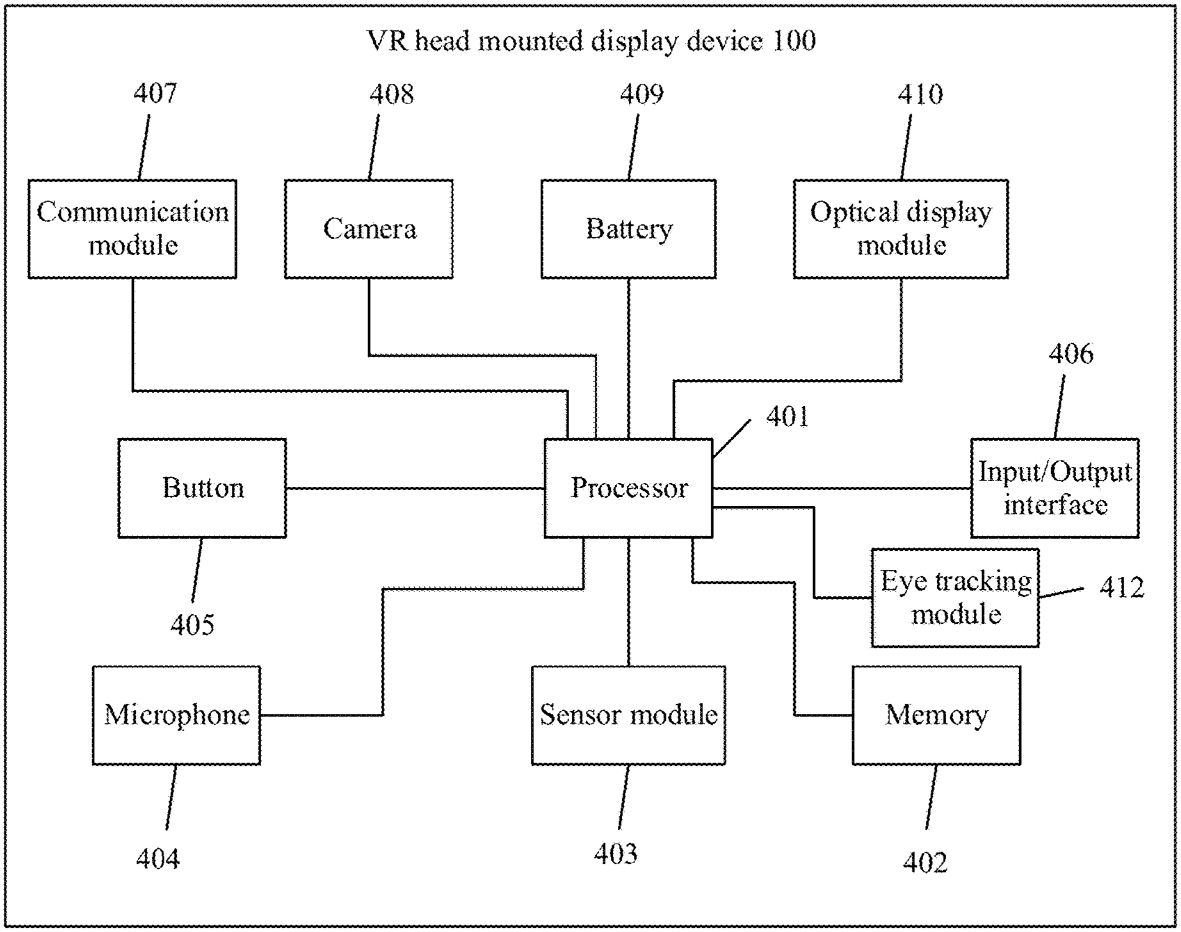
FIG. 4 is a schematic diagram of a structure of a VR head mounted display device according to an embodiment of this disclosure.

It may be understood that the VR head mounted display device 100 may further include more components. For example, FIG. 4 shows a schematic diagram of a structure of a VR head mounted display device 100 according to an embodiment of this disclosure. As shown in FIG. 4, the VR head mounted display device 100 may include a processor 401, a memory 402, a sensor module 403 (which may be configured to obtain a posture of a user), a microphone 404, a button 405, an input/output interface 406, a communication module 407, a camera 408, a battery 409, an optical display assembly 410, an eye tracking module 412, and the like.

It can be understood that, the structure shown in this embodiment of this disclosure does not constitute a specific limitation on the VR head mounted display device 100. In some other embodiments of this disclosure, the VR head mounted display device 100 may include more or fewer components than those shown in the figure, or combine some components, or split some components, or have different component arrangements. The components shown in the figure may be implemented by hardware, software, or a combination of software and hardware.

The processor 401 is usually configured to control an overall operation of the VR head mounted display device 100, and may include one or more processing units. For example, the processor 401 may include an application processor (AP), a modem processor, a graphics processing unit (GPU), an image signal processor (ISP), a video processing unit (VPU), a controller, a memory, a video codec, a digital signal processor (DSP), a baseband processor, a neural-network processing unit (NPU), and/or the like. Different processing units may be independent components, or may be integrated into one or more processors.

A memory may be further disposed in the processor 401, and is configured to store instructions and data. In some embodiments, the memory in the processor 401 is a cache. The memory may store instructions or data that has been used or cyclically used by the processor 401. If the processor 401 uses the instructions or the data again, the processor 401 may directly invoke the instructions or the data from the memory. This avoids repeated access and reduces waiting time of the processor 401, thereby improving system efficiency.

In some embodiments of this disclosure, the processor 401 may obtain a human eye light spot image sent by a camera module in the eye tracking module 412, and may further learn a position of an eye of the user, to calculate a fixation point of the user.

In some embodiments, the processor 401 may include one or more interfaces. The interface may include an inter-integrated circuit (I2C) interface, a universal asynchronous receiver/transmitter (UART) interface, a mobile industry processor interface (MIPI), a general-purpose input/output (GPIO) interface, a subscriber identity module (SIM) interface, and/or a universal serial bus (USB) interface, a serial peripheral interface (SPI) interface, and the like.

The I2C interface is a two-way synchronization serial bus, and includes one serial data line (SDA) and one derail clock line (SCL). In some embodiments, the processor 401 may include a plurality of I2C buses.

The UART interface is a universal serial data bus, and is configured to perform asynchronous communication. The bus may be a two-way communication bus. The bus converts to-be-transmitted data between serial communication and parallel communication. In some embodiments, the UART interface is usually configured to connect the processor 401 and the communication module 407. For example, the processor 401 communicates with a BLUETOOTH module in the communication module 407 by using the UART interface, to implement a BLUETOOTH function.

The MIPI interface may be configured to connect the processor 401 to a peripheral component, for example, a display or the camera 408 in the optical display module 410.

The GPIO interface may be configured by using software. The GPIO interface may be configured as a control signal or a data signal. In some embodiments, the GPIO interface may be configured to connect the processor 401 to the camera 408, the display in the optical display module 410, the communication module 407, the sensor module 403, the microphone 404, and the like. The GPIO interface may alternatively be configured as an I2C interface, an I2S interface, a UART interface, an MIPI interface, or the like. In some embodiments, the camera 408 may collect an image including a real object, and the processor 401 may fuse the image collected by the camera with a virtual object, and obtain an image obtained through real fusion by using the optical display module 410.

The USB port is a port that conforms to a USB standard specification, and may be specifically a mini USB port, a micro USB port, a USB type-C port, or the like. The USB port may be configured to connect to a charger to charge the VR head mounted display device 100, or may be configured to transmit data between the VR head mounted display device 100 and a peripheral device, or may be configured to connect to a headset for playing audio by using the headset. The port may be further configured to be connected to another electronic device, for example, a mobile phone, or the like. The USB port may be a USB 3.0, and is configured to be compatible with a high-speed display port (DP) for signal transmission, and may transmit high-speed audio and video data.

It can be understood that, connection relationships between interfaces of various modules shown in this embodiment of this disclosure are merely an illustrative description, and do not constitute a limitation on a structure of the VR head mounted display device 100. In some other embodiments of this disclosure, the VR head mounted display device 100 may use interface connection manners different from those in the foregoing embodiment, or use a combination of a plurality of interface connection manners.

In addition, the VR head mounted display device 100 may include a wireless communication function. For example, the VR head mounted display device 100 may receive an image from another electronic device (for example, a VR host) for display. The communication module 407 may include a wireless communication module and a mobile communication module. The wireless communication function may be implemented by using an antenna (not shown), the mobile communication module (not shown), a modem processor (not shown), a baseband processor (not shown), and the like. The antenna is configured to transmit and receive an electromagnetic wave signal. The VR head mounted display device 100 may include a plurality of antennas, and each antenna may be configured to cover a single or a plurality of communication bands. Different antennas may be further multiplexed, to improve antenna utilization. For example, one antenna can be multiplexed as a diversity antenna of a wireless local area network. In some other embodiments, the antenna may be used in combination with a tuning switch.

The mobile communication module may provide a wireless communication solution applied to the VR head mounted display device 100, including a 2nd generation (2G) network, a 3rd generation (3G) network, a 4th generation (4G) network, a 5th generation (5G) network, and the like. The mobile communication module may include at least one filter, a switch, a power amplifier, a low noise amplifier (LNA), and the like. The mobile communication module may receive an electromagnetic wave through the antenna, perform processing such as filtering and amplifying on the received electromagnetic wave, and transmit the received electromagnetic wave to the modem processor for demodulation. The mobile communication module may further amplify a signal modulated by the modem processor, and convert the signal into an electromagnetic wave through the antenna and radiate the electromagnetic wave. In some embodiments, at least some function modules in the mobile communication module may be disposed in the processor 401. In some embodiments, at least some function modules of the mobile communication module may be disposed in a same device as at least some modules of the processor 401.

The modem processor may include a modulator and a demodulator. The modulator is configured to modulate a to-be-sent low-frequency baseband signal into a medium-high frequency signal. The demodulator is configured to demodulate a received electromagnetic wave signal into a low-frequency baseband signal. Then the demodulator transfers the low-frequency baseband signal obtained through demodulation to the baseband processor for processing. After being processed by the baseband processor, the low-frequency baseband signal is transmitted to the application processor. The application processor outputs a sound signal by using an audio device (not limited to a speaker or the like), or displays an image or a video by using a display in the optical display module 410. In some embodiments, the modem processor may be an independent component. In some other embodiments, the modem processor may be independent of the processor 401, and is disposed in a same device as the mobile communication module or another function module.

The wireless communication module may provide a solution that is applied to the VR head mounted display device 100 and includes wireless communication including a WLAN (for example, a Wi-Fi network), BLUETOOTH, a Global Navigation Satellite System (GNSS), FM, NFC technology, an IR technology, or the like. The wireless communication module may be one or more devices integrating at least one communication processing module. The wireless communications module receives an electromagnetic wave through an antenna, performs frequency modulation and filtering processing on the electromagnetic wave signal, and sends the processed signal to the processor 401. The wireless communications module may further receive a to-be-sent signal from the processor 401, perform frequency modulation and amplification on the signal, and convert, through the antenna, the signal into an electromagnetic wave for radiation.

In some embodiments, the antenna of the VR head mounted display device 100 is coupled to the mobile communication module, so that the VR head mounted display device 100 may communicate with another device and a network by using a wireless communication technology. The wireless communication technology may include a Global System for Mobile communications (GSM), a General Packet Radio Service (GPRS), code-division multiple access (CDMA), wideband code-division multiple access (WCDMA), time-division code-division multiple access (TD-CDMA), Long-Term Evolution (LTE), BT, a GNSS, a WLAN, NFC, FM, an IR technology, and/or the like. The GNSS may include a Global Positioning System (GPS), a Global Navigation Satellite System (GLONASS), a BeiDou navigation satellite system (BDS), a quasi-zenith satellite system (QZSS), and/or a satellite based augmentation system (SBAS).

The VR head mounted display device 100 implements a display function by using the GPU, the optical display module 410, the application processor, and the like. The GPU is a microprocessor for image processing, and is connected to the optical display module 410 and the application processor. The GPU is configured to: perform mathematical and geometric computation, and render an image. The processor 401 may include one or more GPUs, and the GPUs execute program instructions to generate or change display information.

The memory 402 may be configured to store computer-executable program code, and the executable program code includes instructions. The processor 401 executes various function applications and data processing of the VR head mounted display device 100 by running the instructions stored in the memory 402. The memory 402 may include a program storage region and a data storage region. The program storage region may store an operating system, an application required by at least one function (for example, a voice playing function or an image playing function), and the like. The data storage region may store data (such as audio data and an address book) and the like created during use of the VR head mounted display device 100. In addition, the memory 402 may include a high-speed random access memory, or may include a nonvolatile memory, for example, at least one magnetic disk storage device, a flash memory, a universal flash storage (UFS), or the like.

The VR head mounted display device 100 may implement an audio function by using an audio module, the speaker, the microphone 404, a headset jack, the application processor, and the like, for example, music playing, recording, or the like. The audio module is configured to convert digital audio information into analog audio signal output, and is further configured to convert an analog audio input into a digital audio signal. The audio module may be further configured to code and decode an audio signal. In some embodiments, the audio module may be disposed in the processor 401, or some function modules in the audio module are disposed in the processor 401. The speaker, also referred to as a "loudspeaker", is configured to convert an audio electrical signal into a sound signal. The VR head mounted display device 100 may be used to listen to music or a hands-free call by using the speaker.

The microphone 404, also referred to as a "mike" or a "mic", is configured to convert a sound signal into an electrical signal. At least one microphone 404 may be disposed in the VR head mounted display device 100. In some other embodiments, two microphones 404 may be disposed in the VR head mounted display device 100, to implement a noise reduction function in addition to collecting a sound signal. In some other embodiments, three, four, or more microphones 404 may be disposed in the VR head mounted display device 100, to collect a sound signal and implement noise reduction, and further recognize a sound source to implement a directional recording function and the like.

The headset jack is configured to connect to a wired headset. The headset jack may be a USB port, or may be a 3.5 millimeter (mm) Open Mobile Terminal Platform (OMTP) standard interface or a CTIA standard interface.

In some embodiments, the VR head mounted display device 100 may include one or more buttons 405. These buttons may control a VR wearable device, and provide a user with a function of accessing the VR head mounted display device 100. The buttons 405 may be in a form of a button, a switch, a dial, or a touch or near-touch sensing device (for example, a touch sensor). Specifically, for example, the user may enable the optical display module 410 of the VR head mounted display device 100 by pressing the button. The button 405 includes a power button, a volume button, and the like. The button 405 may be a mechanical button, or may be a touch button. The VR head mounted display device 100 may receive an input from the button, and generate a button signal input related to user settings and function control of the VR head mounted display device 100.

In some embodiments, the VR head mounted display device 100 may include an input/output interface 406, and the input/output interface 406 may connect another apparatus to the VR head mounted display device 100 by using a proper component. The component may include, for example, an audio/video jack, a data connector, and the like.

The optical display module 410 is configured to present an image to the user under control of the processor 401. The optical display module 410 may convert, by using one or more optical devices of a reflection mirror, a transmission mirror, an optical waveguide, or the like, a real pixel image into a near-eye projected virtual image for display, to implement virtual interaction experience or implement interaction experience combining virtual and reality. For example, the optical display module 410 receives image data information sent by the processor 401, and presents a corresponding image to the user. In some embodiments, the optical display module 410 may include an optical display module 210 and an optical display module 220.

In this embodiment of this disclosure, the VR head mounted display device 100 further includes an eye tracking module 412. The eye tracking module 412 is configured to track movement of a human eye, to determine a fixation point of the human eye. For example, by using an image processing technology, a pupil position may be located, and pupil center coordinates may be obtained, to calculate a fixation point of a person. In some embodiments, the eye tracking system may determine a fixation point position of the user (or determine a line-of-sight direction of the user) by using a method, for example, a video eye pattern method, a photoelectric diode response method, or a pupil-cornea reflection method, to implement eye tracking of the user.

It should be noted that, in some embodiments of this specification, an eye tracking module corresponding to each eye of the user may be separately disposed, to synchronously or asynchronously perform eye tracking on the eyes. In some other embodiments of this specification, an eye tracking module may alternatively be disposed only near a single eye of the user, a line-of-sight direction corresponding to the human eye is obtained by using the eye tracking module, and a line-of-sight direction or a fixation position of the other eye of the user may be determined based on a relationship between fixation points of the two eyes (for example, when the user observes an object by using the two eyes, the fixation points of the two eyes are generally close or the same) and a distance between the two eyes of the user.

It can be understood that, the structure shown in this embodiment of this disclosure does not constitute a specific limitation on the VR head mounted display device 100. In some other embodiments of this disclosure, the VR head mounted display device 100 may include more or fewer components than those shown in the FIG. 2A, or combine some components, or split some components, or have different component arrangements. This is not limited in this embodiment of this disclosure.

It may be understood that the VR head mounted display device 100 is an example of the electronic device in this embodiment of this disclosure. The electronic device in this embodiment of this disclosure may further have many other forms, for example, an AR wearable device, an MR wearable device, an in-vehicle eye tracking display apparatus, a smart mobile device, a large-screen display, an intelligent vehicle, a computer monitor, and the like. This is not limited herein.

Figure 5:
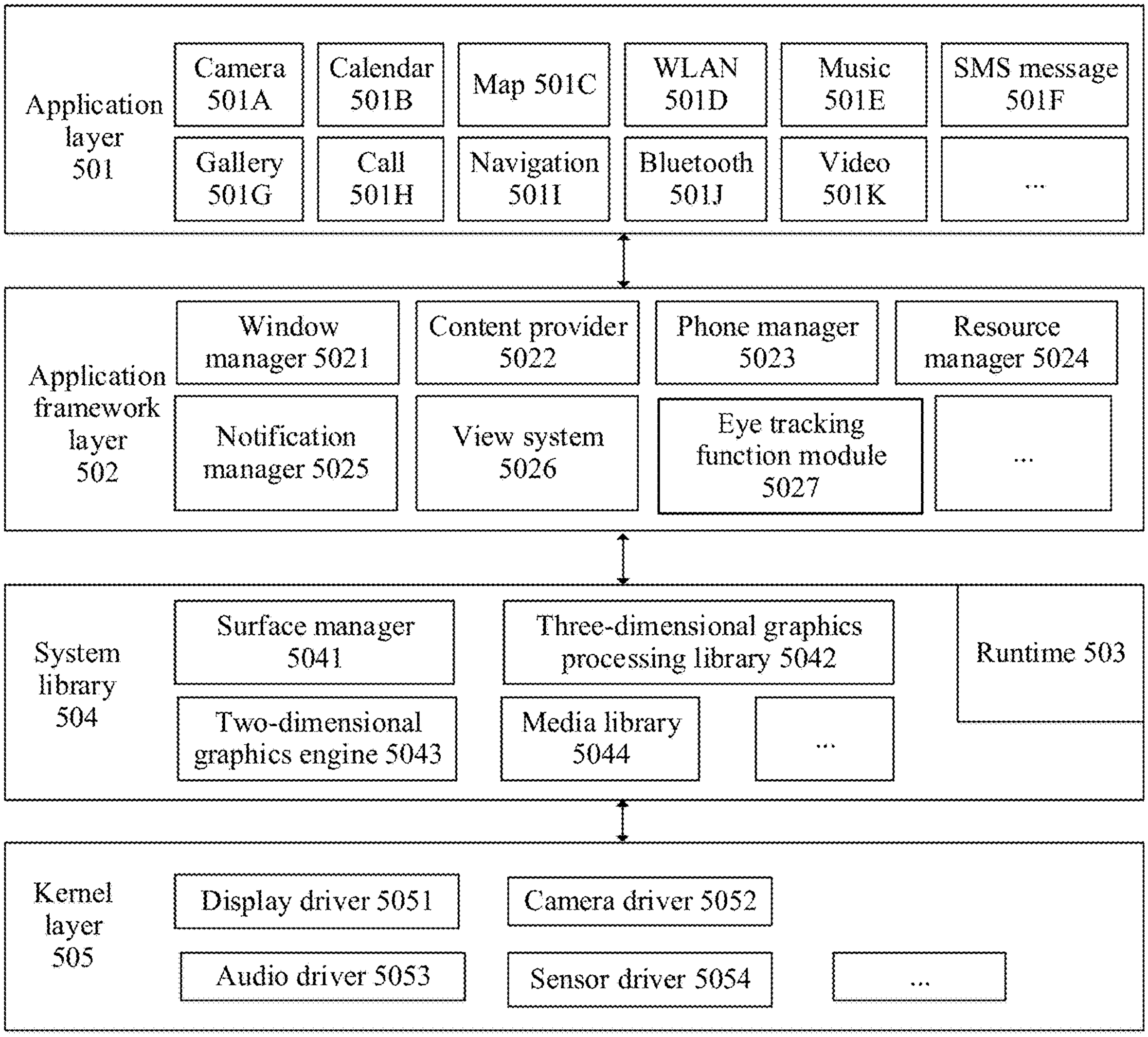
FIG. 5 is a block diagram of an example of a software structure of a VR head mounted display device according to an embodiment of this disclosure.

FIG. 5 is a block diagram of an example of a software structure of the VR head mounted display device 100 according to an embodiment of this disclosure.

In a layered architecture, software is divided into several layers, and each layer has a clear role and task. The layers communicate with each other through a software interface. In some embodiments, a system is divided into four layers: an application layer 501, an application framework layer 502, a runtime 503 and a system library 504, and a kernel layer 505 from top to bottom.

The application layer 501 may include a series of application packages.

As shown in FIG. 5, the application package may include applications (which may also be referred to as applications) such as a camera application 501A, a calendar application 501B, a map application 501C, a WLAN application 501D, a music application 501E, a short message service (SMS) message application 501F, a gallery application 501G, a call application 501H, a navigation application 501I, a Bluetooth application 501J, and a video application 501K.

The application framework layer 502 provides an application programming interface (API) and a programming framework for the application at the application layer. The application framework layer includes some predefined functions.

As shown in FIG. 5, the application framework layer 502 may include a window manager 5021, a content provider 5022, a phone manager 5023, a resource manager 5024, a notification manager 5025, a view system 5026, and the like.

The window manager 5021 is configured to manage a window program. The window manager 5021 may obtain a size of a display, determine whether there is a status bar, perform screen locking, take a screenshot, and the like.

The content provider 5022 is configured to store and obtain data, and enable the data to be accessed by an application. The data may include a video, an image, audio, calls that are made and answered, a browsing history and bookmarks, an address book, and the like.

The phone manager 5023 is configured to provide a communication function of the VR head mounted display device 100, for example, management of a call status (including answering, declining, or the like).

The resource manager 5024 provides various resources such as a localized character string, an icon, an image, a layout file, and a video file for an application.

The notification manager 5025 enables an application to display notification information in a status bar, and may be used to convey a notification message. The notification manager may automatically disappear after a short pause without requiring user interaction. For example, the notification manager is configured to notify download completion, give a message notification, and the like. The notification manager may alternatively be a notification that appears in a top status bar of the system in a form of a graph or a scroll bar text, for example, a notification of an application running on the background, or may be a notification that appears on the display in a form of a dialog interface. For example, text information is displayed in the status bar, an announcement is given, the electronic device vibrates, or an indicator light blinks.

The view system 5026 includes a visual control, for example, a control for displaying a text and a control for displaying an image. The view system may be configured to construct an application. A display interface may include one or more views. For example, a display interface including an SMS message notification icon may include a text display view and an image display view.

The runtime 503 includes a core library and a virtual machine. The runtime is responsible for scheduling and management of the system.

The core library includes two parts: a performance function that is invoked by a programming language (for example, Java language), and a system core library.

The application layer 501 and the application framework layer 502 run on the virtual machine. The virtual machine executes programming files (for example, Java files) of the application layer 501 and the application framework layer 502 as binary files. The virtual machine is configured to implement functions such as object lifecycle management, stack management, thread management, security and exception management, and garbage collection.

The system library 504 may include a plurality of function modules, for example, a surface manager 5041, a three-dimensional graphics processing library 5042 (for example, Open Graphics Library for Embedded Systems (OpenGL ES)), a two-dimensional graphics engine 5043 (for example, Simple Graphics Library (SGL)), a media library 5044, and the like.

The surface manager 5041 is configured to: manage a display subsystem and provide fusion of two-dimensional (2D) and three-dimensional (3D) layers for a plurality of applications.

The media library 5044 supports playback and recording in a plurality of commonly used audio and video formats, and static image files. The media library may support a plurality of audio and video coding formats, for example, Motion Picture Experts Group 4 (MPEG-4), H.264, MPEG-1 Audio Layer 3 (MP3), Advanced Audio Coding (AAC), Adaptive Multi-Rate (AMR), Joint Photographic Experts Group (JPG), Portable Network Graphics (PNG), and the like.

The three-dimensional graphics processing library 5042 is configured to implement 3D graphics drawing, image rendering, composition, layer processing, and the like.

The two-dimensional graphics engine 5043 is a drawing engine for 2D drawing.

The kernel layer 505 is a layer between hardware and software. The kernel layer 505 includes at least a display driver 5051, a camera driver 5052, an audio driver 5053, and a sensor driver 5054.

In some embodiments of this disclosure, the application framework layer 502 may further include an eye tracking function module 5027 configured to: match a light spot in a human eye image obtained by the camera driver 5052 with a light source, and calculate a line-of-sight direction of a user, to determine a fixation point of the user. In some other embodiments of this disclosure, the eye tracking function module 5027 may alternatively be located at the application layer 501, the system library 504, or the kernel layer 505. This is not limited herein.

Figure 6:
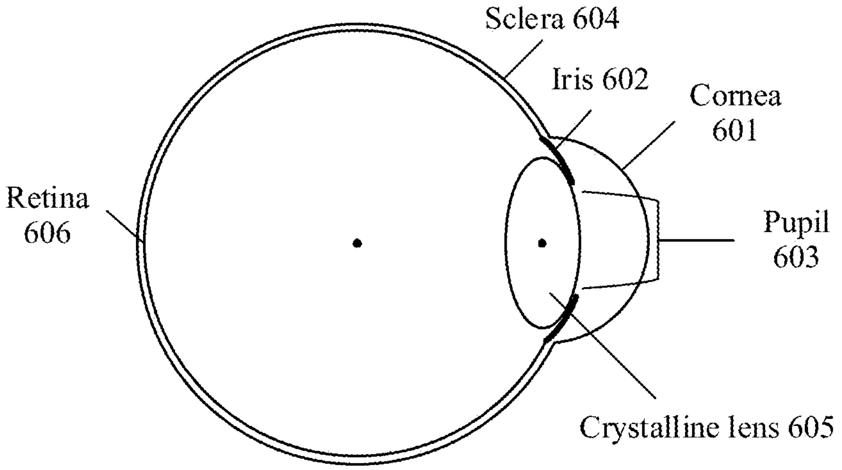
FIG. 6 is a schematic cross-sectional diagram of an eyeball structure model according to an embodiment of this disclosure.

FIG. 6 is a schematic cross-sectional diagram of an eyeball structure model according to an embodiment of this disclosure. As shown in FIG. 6, the eyeball includes a cornea 601, an iris 602, a pupil 603, a sclera 604, a crystalline lens 605, and a retina 606.

The cornea 601 has a high reflectivity of light irradiated by the light source. Therefore, a clear reflection point can be formed after the light source performs irradiation. The cornea 601 is a transparent part of the front part of the eyeball, and is a first gateway for light to enter the eyeball. About 3 mm on a center of an outer surface of the cornea 601 is a spherical arc surface, and is referred to as an optical region. A curvature radius of a periphery gradually increases, and is in an aspheric shape. In the eyeball structure model shown in FIG. 6, it is assumed that the cornea 601 is a spherical arc surface.

Because the iris 602 covered by the cornea 601 is a disk-shaped membrane, a region in which the iris 602 is located is a dark-color circle, and there is a hole in the center, which is referred to as the pupil 603. If light is too strong, an enclave muscle in the iris 602 shrinks, and the pupil 603 shrinks; or if the light becomes weak, an open muscle of the iris 602 shrinks, and the pupil 603 becomes larger. The pupil 603 is a small circular hole in the center of the iris in eyes of an animal or a human, and is a channel through which light enters the eyes. The crystalline lens 605 is a double-convex transparent tissue located behind the iris 602. A shape and a function of the crystalline lens 605 are similar to those of a convex lens, and can clearly reflect an image of a distant object on the retina 606. The retina 606 is a photosensitive part of the eyeball, and an external object is imaged on the retina 606.

The sclera 604 (also referred to as white of the eye) has a low reflectivity to light irradiated by the light source. The sclera 604 is one of main components of an eyeball wall, located at a junction with the cornea, and has a tough structure to support and protect an intraocular tissue.

Figure 7:
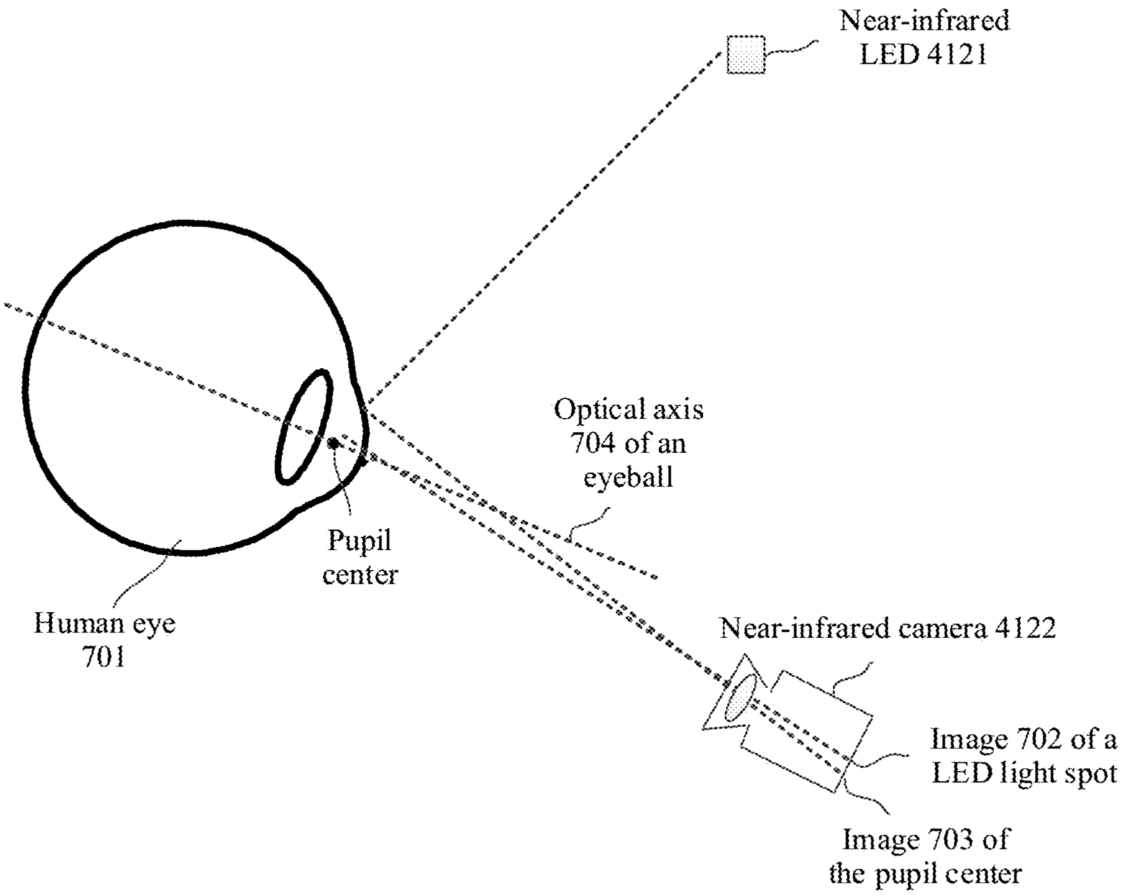
FIG. 7 is a schematic diagram of an example in which an eye tracking module in a VR head mounted display device implements eye tracking by using a pupil-cornea reflection method.

FIG. 7 is a schematic diagram of an example in which the eye tracking module 412 in the VR head mounted display device 100 implements eye tracking by using a pupil-cornea reflection method. The eye tracking module 412 may include one or more light sources 4121 and one or more camera modules 4122. In FIG. 7, an example in which the light source 4121 is a near-infrared LED 4121 is used for description, and an example in which the camera module 4122 is a near-infrared camera 4122 is used for description. When light emitted by the light source is invisible light (for example, infrared light emitting or near-infrared light emitting), impact of the light source on an eye can be avoided, and eye tracking without perception can be performed.

In some embodiments, the eye tracking module 412 may obtain a fixation direction of a user by using the following method: The near-infrared LED 1201 irradiates a human eye 701, light of the near-infrared LED 4121 is irradiated to the human eye, and is reflected in a region, for example, a cornea 601 or an iris 602 of the human eye. The near-infrared camera 4122 may obtain reflected light and a human eye image, to obtain a human eye light spot image. In some embodiments, the near-infrared camera 4122 may obtain an image 702 (for example, an image of a light spot) of reflected light and an image of a human eye (the image of the human eye includes an image 703 of a pupil center). The human eye light spot image includes the image 702 (for example, the image of the light spot) of the reflected light and the image of the human eye. An optical axis direction 704 of the eyeball may be determined based on the human eye light spot image, to obtain a line-of-sight direction of the user.

In some embodiments, a process of obtaining the fixation direction of the user may be divided into the following stages.

(1) Calibrating a Human Eye Parameter

Because eyeballs of each user are different, human eye parameters tracked and used in the calculation process of pupil-cornea reflection are different. To improve precision of a final calculation result, a human eye parameter is calibrated before an algorithm of the pupil-cornea reflection method is used for calculation, and a calibrated human eye parameter is obtained for subsequent algorithm solving.

A human eye parameter calibration result includes an included angle between a visual axis direction of the user and an optical axis direction. The visual axis direction is the fixation direction of the user, and the optical axis direction is a direction from the pupil center of the user's eyes to a corneal center.

(2) Detecting the Light Spot and the Pupil on an Image

After the light source 4121 in the eye tracking module 412 is used to irradiate the human eye, the human eye reflects a part of light irradiated by the light source 4121 to the camera module 4122 in the eye tracking module 412, and the camera module 4122 may obtain a human eye light spot image.

Figure 8:
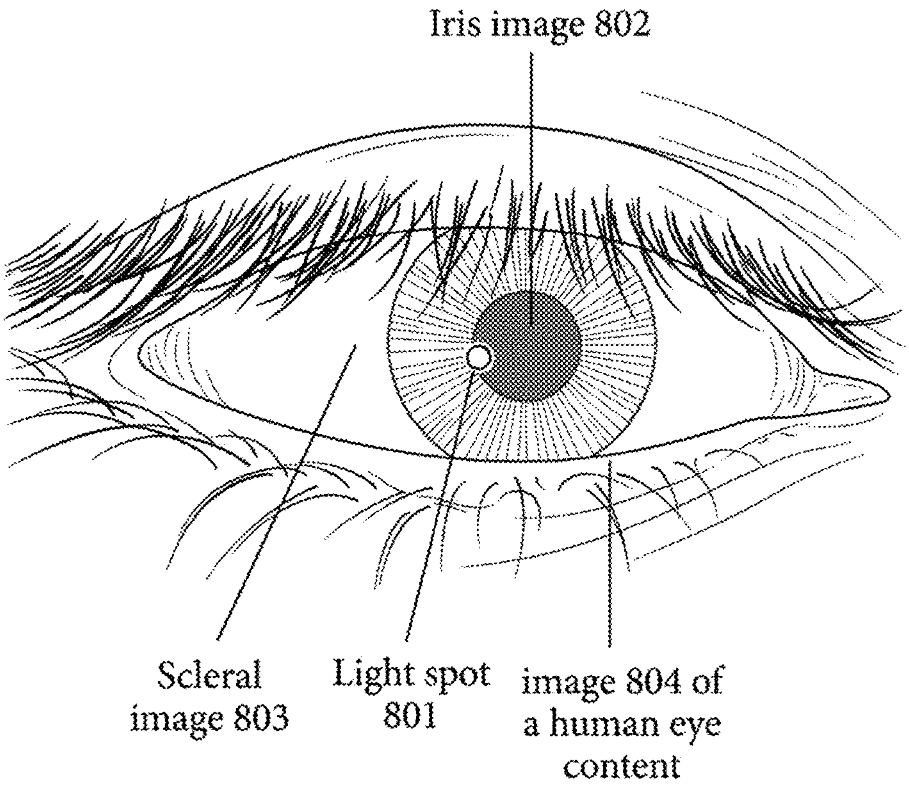
FIG. 8 is a schematic diagram of an example of a human eye light spot image according to an embodiment of this disclosure.

FIG. 8 is a schematic diagram of an example of a human eye light spot image. The human eye light spot image may include: a light spot 801, which is an image of a reflection point of the camera module 4122 by reflected light obtained after the light source 4121 irradiates a region of the cornea 601 of the human eye; an iris image 802, which is formed by scattering light to the camera module 4122 after the light source 4121 irradiates a region of the iris 602 of the human eye; a scleral image 803, which is formed by scattering light to the camera module 4122 after the light source 4121 irradiates a region of the sclera 604 of the human eye; and a human eye contour image 804, which is formed by scattering light to the camera module 4122 after the light source 4121 irradiates a human eye contour. The human eye light spot image may further include images such as a center of the pupil 603 (not shown in the figure), an eye hair, and an eye skin that are located in a center of the region of the iris 602.

In FIG. 8, the light spot 801 in the human eye light spot image is located in a region of the iris image 802. Because in a human eye structure, the cornea 601 has a high reflectivity, and the transparent cornea 601 covers the iris 602, all light spots formed by light reflected by the cornea 601 or the iris 602 are located in the region of the iris image 802. In addition, because a reflectivity of the sclera 604 is low, it is difficult for the camera module 4122 to capture a light spot formed by light reflected by the sclera 604.

After the human eye light spot image is obtained, the VR head mounted display device 100 performs high-precision detection on the human eye light spot image to determine positions of the light spot and the pupil center in the human eye light spot image.

(3) Matching the Light Spot and a Light Source

After the positions of the light spot and the pupil center on the human eye light spot image are detected, if a pupil-cornea reflection method is used for subsequent calculation, the light spot detected on the human eye light spot image is matched to a light source in the three-dimensional physical world, that is, a light source from which the light spot on the human eye light spot image is formed by light reflection is found.

(4) Calculating Positions of a Membrane Center and the Pupil Center in Three-Dimensional Physical Space, to Determine the Optical Axis Direction After completing matching the light spot in the human eye light spot image with the light source 4121 of the eye tracking module 412 in the three-dimensional physical space, the VR head mounted display device 100 may calculate, by using a subsequent algorithm, the positions of the corneal center and the pupil center of the user in the three-dimensional physical space. A connection line between the corneal center and the pupil center is used as the optical axis of the human eye of the user when the human eye light spot image is obtained. In this way, the optical axis direction is obtained through calculation.

(5) Obtaining the Visual Axis Direction Based on the Human Eye Parameter and the Optical Axis Direction, that is, the Line-of-Sight Direction of the User.

Based on the optical axis direction of the eye of the user that is obtained in (4) and the included angle between the optical axis direction of the eye of the user and the visual axis direction that is obtained in (1), the visual axis direction of the eye of the user, that is, the fixation direction of the eye of the user, may be obtained through calculation. The fixation direction of the eye of the user can further be used to calculate the fixation point of the user on the display.

Figure 9:
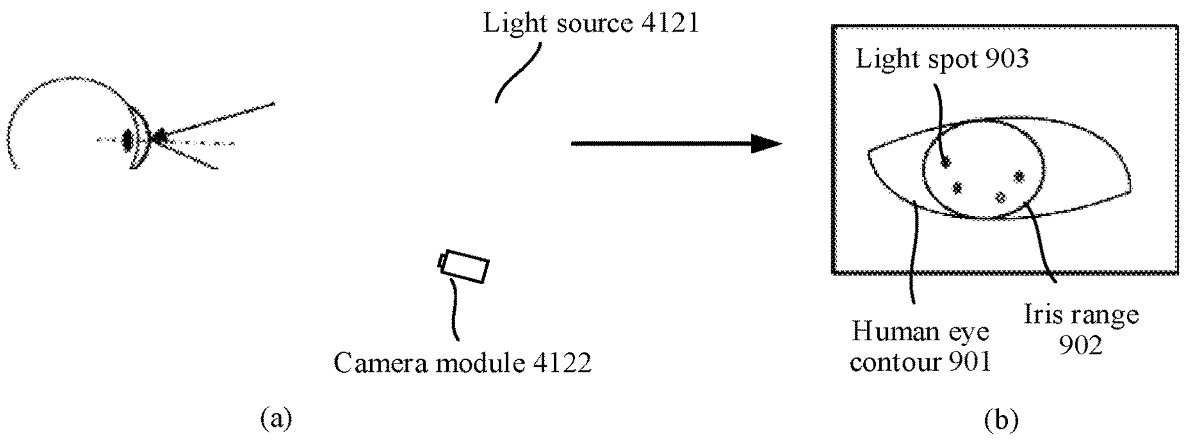
FIG. 9 is a schematic diagram of a scenario in which a light source irradiates an eye to obtain a human eye light spot image according to an embodiment of this disclosure.

With reference to the VR head mounted display device 100 shown in FIG. 2A, FIG. 9 is a schematic diagram of a scenario in which the light source 4121 irradiates an eye to obtain a human eye light spot image. Disposition manners and positions of the light source 4121 and the camera module 4122 in FIG. 9 may be shown in FIG. 2A. As shown in FIG. 9, only a case of one eye is taken for description. A coordinate system shown in (a) in FIG. 9 is a rectangular coordinate system established by using a center point of a surface (for example, a surface 210*a*) on which eight light sources 4121 are located as an origin. The rectangular coordinate system is established herein only for calibrating a position of each component for ease of description. In actual application, the VR head mounted display device 100 may establish a coordinate system, or may not establish a coordinate system. This is not limited herein. The camera module 4122 is in the lower right corner of the coordinate system. In a physical process in which light emitted by the eight light sources 4121 is irradiated to the eye and the camera module 4122 performs imaging, the light is further refracted by a series of lenses in a camera lens of the camera module 4122. In some embodiments, a quantity of light spots is less than or equal to a quantity of light sources. As shown in (b) in FIG. 9, the finally obtained human eye light spot image may include a human eye contour 901, an iris range 902, and four light spots 903.

In this case, it is difficult to determine that the four light spots 903 are generated by reflected light of light emitted by which light sources in the eight light sources 4121. If the light spot cannot be accurately matched with the light source, the fixation point of the human eye cannot be accurately determined.

(b) in FIG. 9 is used as an example. The quantity of light spots 903 is less than the quantity of light sources, and a reason may include one or more of the following aspects.

1. Due to rotation of the human eyeball, positions of reflection points obtained by a light source at a known position in space irradiates the human eye are different. As shown in FIG. 6, because the cornea 601 has a high reflectivity, and the sclera 604 has a low reflectivity, when a reflection point of light that is of the light source 4121 and that is irradiated to the eye is on the sclera 604, the camera module 4122 may not capture the light spot. Consequently, the quantity of light spots in the obtained image is less than the actual quantity of light sources.

2. When the human eye rotates to a specific angle, because light emitted by the light sources 4121 at different positions is reflected or refracted differently, reflection points of two or more light sources 4121 may overlap in a reflection process of the human eye. That is, one light spot 903 on the human eye light spot image obtained by the camera module 4122 may correspond to a plurality of light sources.

3. To avoid blocking the lens group, the camera module 4122 is biased, that is, the camera module 4122 is not in a center of the plurality of light sources 4121, and light of the light source 4121 is refracted for a plurality of times when reaching the image sensor of the camera module 4122, and an optical path is complex.

Therefore, in this case, ambiguity may occur when the light spot is matched with the light source, that is, one light spot may correspond to a plurality of light sources, and not all light sources correspond to light spots, and it is impossible to accurately distinguish a light source or light sources each light spot corresponds to.

However, by using the eye tracking module 412 provided in this embodiment of this disclosure, matching between the light source and the light spot can be performed more quickly and accurately, thereby eliminating ambiguity.

For brevity of description and ease of understanding, in this embodiment of this disclosure, a structure of the eye tracking module 412 that performs eye tracking on a fixation direction of one eye is separately described.

Figure 10:
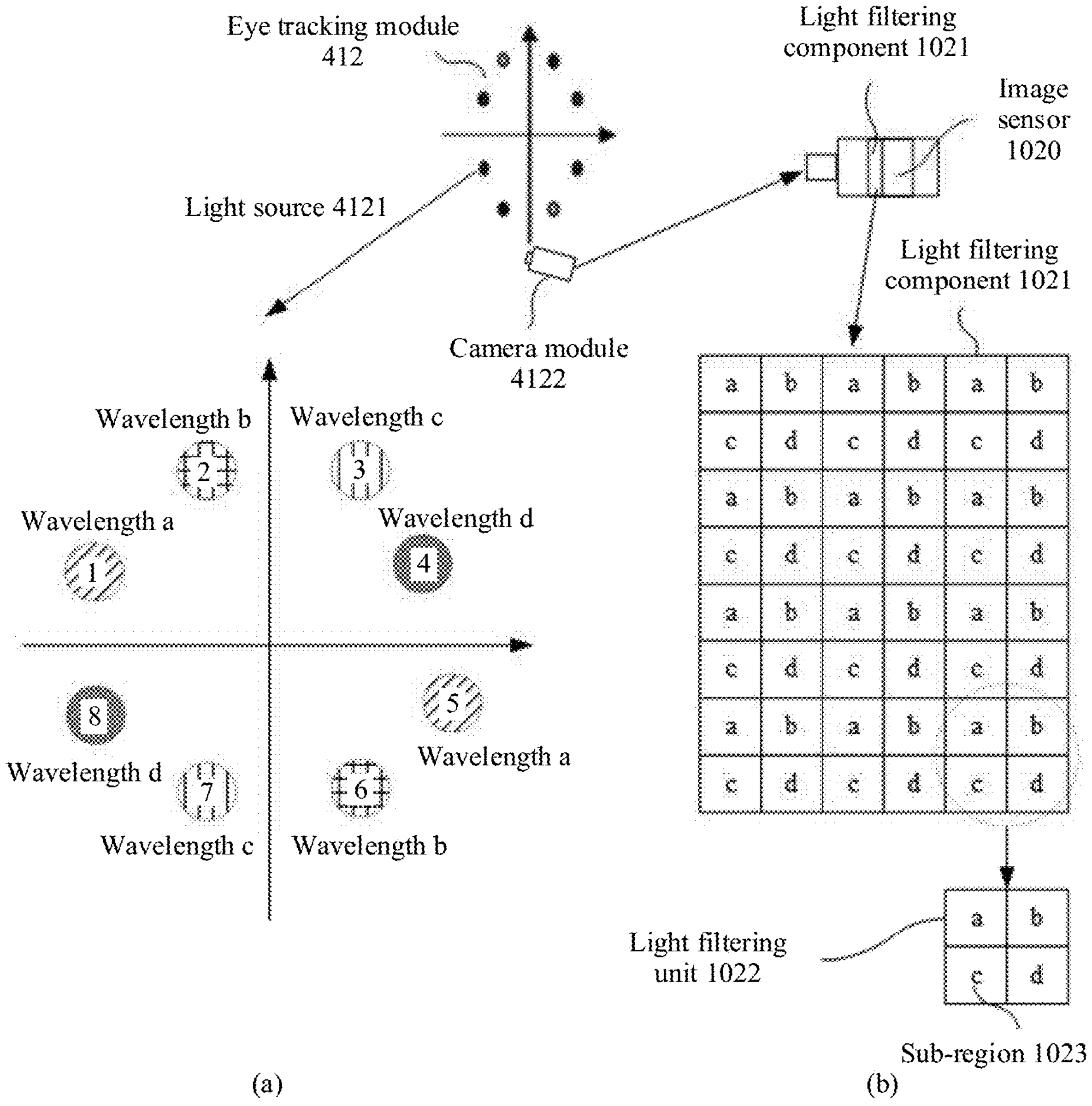
FIG. 10 is a schematic diagram of an example of a light source and a filter on a sensor of a camera module in an eye tracking module according to an embodiment of this disclosure.

For example, FIG. 10 is a schematic diagram of an example of the light source 4121 and a filter on a sensor of the camera module 4122 in the eye tracking module 412 according to an embodiment of this disclosure. The eye tracking module 412 includes the light source 4121 and the camera module 4122. The camera module 4122 includes the camera lens and an image sensor 1020. A light filtering component 1021 is disposed in the image sensor 1020. In some embodiments, the light filtering component 1021 may be a physical device for filtering light in a physical manner. In the example shown in FIG. 10, the light filtering component 1021 is formed by using a process such as etching on a filter. In some embodiments, the light filtering component 1021 may include a plurality of light filters.

In some embodiments, as shown in (a) in FIG. 10, the eye tracking module 412 includes eight light sources 4121, which are respectively a light source 1 to a light source 8. The eight light sources 4121 include four types of light sources, that is, the eight light sources 4121 form four groups of light sources, and light sources in each group of light sources are light sources of a same type. In some implementations, one light source may emit one type of light. Generally, one light source does not emit more than two types of light. In some embodiments, different types of light may be light with different wavelengths, and therefore, N different types of sub-regions may filter the light with different wavelengths. In other embodiments, different types of light may alternatively be light with different modulations. For example, different types of light have different vibration directions, and therefore, N different types of sub-regions may filter the light with different vibration directions. In some implementations, different types of sub-regions may be formed on a same optical element by using different etching processes. For example, when different types of sub-regions may be formed by different filters, different etching patterns may be formed on different sub-regions on a large filter by using an etching process, to form different filtering effect in different sub-regions, so that different sub-regions can transmit light with different wavelengths. For ease of description, the following uses an example in which the different types of light may be light with different wavelengths for description. For example, the light source 1 and the light source 5 are a group of light sources, and light emitting wavelengths of the light source 1 and the light source 5 are both a; the light source 2 and the light source 6 are a group of light sources, and light emitting wavelengths of the light source 2 and the light source 6 are b; the light source 3 and the light source 7 are a group of light sources, and light emitting wavelengths of the light source 3 and the light source 7 are c; and the light source 4 and the light source 8 are a group of light sources, and light emitting wavelengths of the light source 4 and the light source 8 are d.

As shown in (b) in FIG. 10, the light filtering component 1021 is formed by a light filtering unit 1022. For example, the light filtering component 1021 is formed by an array of a plurality of light filtering units 1022, and the light filtering unit 1022 is formed by four sub-regions 1023 that can filter light with the wavelength a, the wavelength b, the wavelength c, and the wavelength d respectively. In this embodiment of this disclosure, filtering light with a wavelength may indicate that only light with the wavelength can pass through the sub-region. For example, a sub-region for filtering the light with the wavelength a indicates that only the light with the wavelength a can pass through the sub-region.

Figure 11:
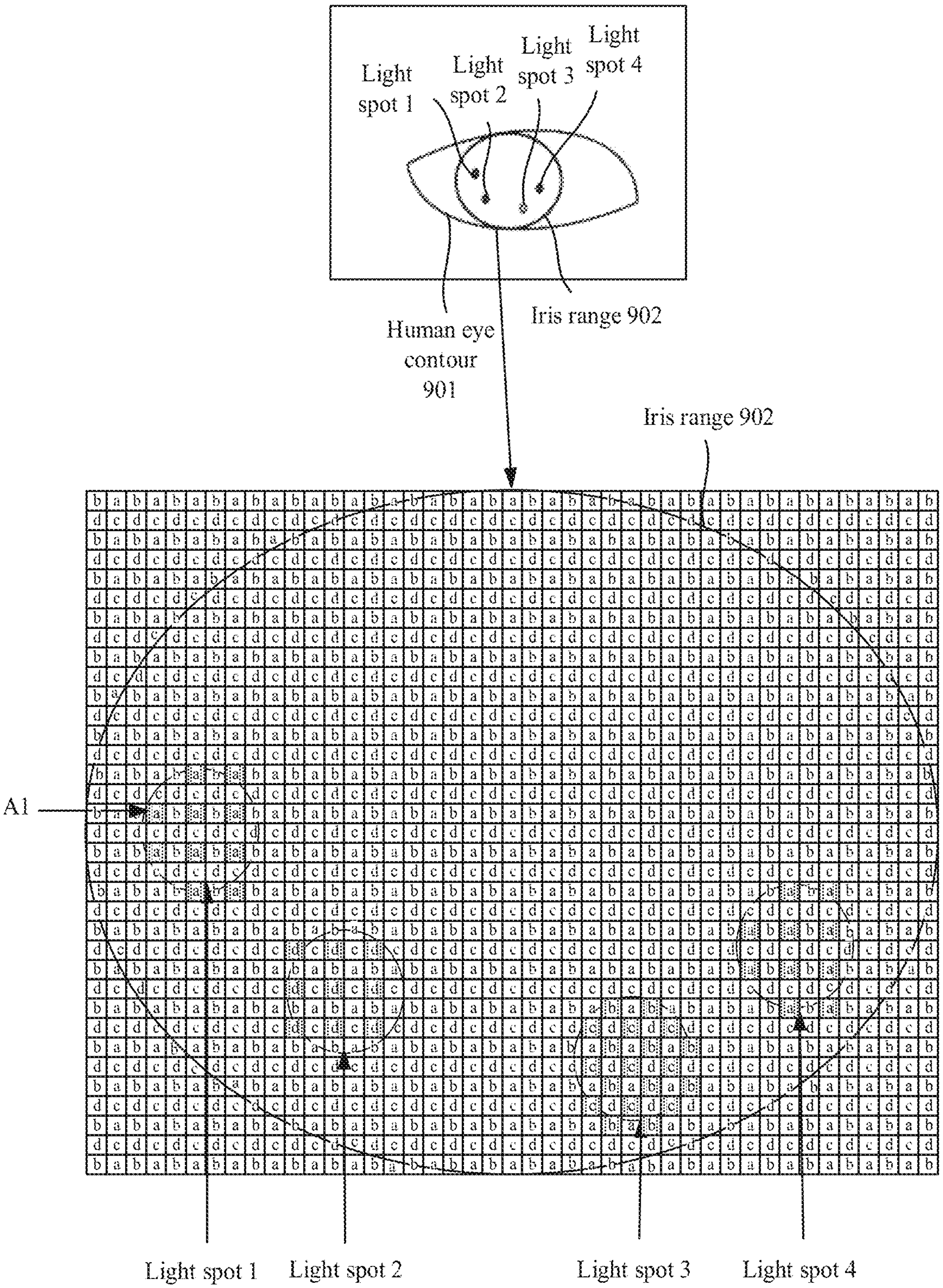
FIG. 11 is a schematic diagram of another example of an obtained human eye light spot image according to an embodiment of this disclosure.

For example, FIG. 11 is a schematic diagram of an example of a human eye light spot image obtained by using the eight light sources 4121 shown in (a) in FIG. 10 to irradiate the human eye and by using the camera module 4122 including the light filter shown in (b) in FIG. 10. The human eye light spot image includes the human eye contour 901, and the iris range 902 includes four light spots: a light spot 1, a light spot 2, a light spot 3, and a light spot 4.

The camera module 4122 uses the light filtering component 1021 that includes the sub-regions that respectively filter the wavelength a, the wavelength b, the wavelength c, and the wavelength d. Therefore, the light spot in the human eye light spot image obtained by the camera module 4122 includes a bright sub-region and a dark sub-region. The dark sub-region is formed because no corresponding light (for example, infrared light with a corresponding wavelength) in the sub-region passes through the sub-region in the light filtering component 1021 and is irradiated to the image sensor 1020. The bright sub-region is formed by corresponding light (for example, infrared light with a corresponding wavelength) passing through the sub-region in the light filtering component 1021 and is irradiated on the image sensor 1020. In some embodiments, because light of different types is light with different wavelengths, the human eye light spot image may be captured in one video frame, so that light source matching can be quickly and accurately performed. In some embodiments, the image sensor has an array of pixels, and the array of pixels may be arranged on the image sensor in a specific manner. The image sensor may be a color image sensor or a black-and-white image sensor. In some embodiments, there is a correspondence between a position, a size, and/or a shape of a sub-region and a pixel of the image sensor 1020, to ensure that whether there is corresponding light passing through each sub-region can be reflected by the image sensor 1020, thereby helping improve accuracy of eye tracking. In FIG. 11, for ease of description, an example in which a position of a sub-region matches a position of a pixel of the image sensor 1020, and a size and a shape of a sub-region are the same as those of a pixel in a corresponding position is used for description. In another embodiment, a position, a size, and/or a shape of the sub-region may alternatively be different from those of the pixel of the image sensor 1020.

In FIG. 11, each sub-region of the light filtering component 1021 corresponds to the iris range 902 including a light spot in the human eye light spot image, where at least within the iris range, each sub-region corresponds to one pixel. In each corresponding sub-region in the human eye light spot image, a pixel filled with a pattern (for example, a shadowed region A1) indicates that light with a corresponding wavelength passes through a sub-region corresponding to the pixel, and a pixel not filled with a pattern indicates that light with a corresponding wavelength does not pass through a sub-region corresponding to the pixel.

For example, the light spot 1 is formed in the image sensor 1020 by light with the wavelength a by passing through the light filtering component 1021. A region in which the light spot 1 is located corresponds to a plurality of sub-regions. As shown in FIG. 11, the region in which the light spot 1 is located corresponds to a plurality of sub-regions that filter the wavelength a, a plurality of sub-regions that filter the wavelength b, a plurality of sub-regions that filter the wavelength c, and a plurality of sub-regions that filter the wavelength d, where no light passes through the sub-regions that filter the wavelength b, the sub-regions that filter the wavelength c, or the sub-regions that filter the wavelength d, and light with the wavelength a passes through the sub-regions that filter the wavelength a, so that pixels that are of the image sensor 1020 and that correspond to the plurality of sub-regions that filter the wavelength a (for example, the shadowed region A1) are bright, thereby forming the light spot 1. Likewise, the light spot 2 is formed by light with the wavelength d by passing through the light filtering component 1021, the light spot 3 is formed by light with the wavelength c and light with the wavelength b by passing through the light filtering component 1021, and the light spot 4 is formed by light with the wavelength a by passing through the light filtering component 1021. Therefore, an order of the wavelengths forming the light spot 1 to the light spot 4 in the human eye light spot image is as follows: the wavelength a, the wavelength d, the wavelength c and the wavelength b, and the wavelength a.

Generally, there is a correspondence between a spatial position of a light spot and a spatial position of a light source, and a relative position between light spots is generally consistent with a relative position between light sources, so that a light source corresponding to each of the light spot 1 to the light spot 4 can be conveniently and accurately learned based on the human eye light spot image. A specific light source of which reflected light is obtained by the image sensor 1020 and a specific pixel at which the image sensor 1020 obtains the reflected light are related to a fixation direction of an eye, so that a fixation point of the eye can be accurately learned.

It should be noted that a specific correspondence between a spatial position of a light spot and a spatial position of a light source is related to an optical structure of a lens that is set based on an actual requirement. For example, in some embodiments, a light spot close to the bottom in the human eye light spot image is usually obtained by irradiation and reflection by a light source closer to the ground. In some embodiments, there is an optical structure that may be used to achieve that a light spot close to the bottom in the human eye light spot image is usually obtained by irradiation and reflection by a light source farther from the ground. This is not limited herein.

For example, in the embodiment shown in FIG. 11, the light spot close to the bottom in the human eye light spot image is usually obtained by irradiation and reflection of a light source closer to the ground. Therefore, it can be quickly and accurately determined that the light spot 1 is obtained by irradiation of the light source 1, and therefore, the light spot 1 matches the light source 1; the light spot 2 is obtained by irradiation of the light source 8, and therefore, the light spot 2 matches the light source 8; the light spot 3 is obtained by irradiation or the light source 7 and the light source 6, and therefore, the light spot 3 matches the light source 7 and the light source 6; and the light spot 4 is obtained by irradiation of the light source 5, and therefore, the light spot 4 matches the light source 5. That is, the light spot 1, the light spot 2, the light spot 3, and the light spot 4 respectively match the light source 1, the light source 8, the light source 7 and the light source 6, and the light source 5.

In this way, the eye tracking module 412 shown in FIG. 10 is used to obtain the human eye light spot image, so that ambiguity in a process of matching a light source with a light spot can be eliminated more quickly and accurately, and a light source or light sources corresponding to each light spot can be accurately distinguished, thereby helping subsequently determine a fixation point of a user more quickly and accurately.

In the foregoing embodiment, based on a type of light that can be filtered in a sub-region corresponding to a bright sub-region in the light spot in the light filtering unit, the light spot in the human eye light spot image is matched with the light source in the eye tracking module 412 with reference to the types of light emitted by the light sources, the relative position between the light spots in the human eye light spot image, and the relative position between the light sources.

It may be understood that, in some embodiments, if types of light emitted by light sources are different from each other, based on only a type of light that can be filtered in a sub-region corresponding to a bright sub-region in the light spot in the light filtering unit, the light source can be alternatively matched with the light spot with reference to the types of light emitted by the light sources.

In some embodiments, if the light source includes more than two (including two) light sources that emit light of a same type, the light sources that emit light of the same type may be controlled to emit light at different moments, or the light sources that emit light of the same type emit light at different frequencies, to further distinguish the light sources. For example, the light sources that emit light of the same type alternately emit light at a first frequency, and the camera module obtains X human eye light spot images at a second frequency greater than or equal to the first frequency, where X is greater than or equal to 2, and the X human eye light spot images include human eye light spot images obtained by the camera module when each of the light sources that emit light of the same type emits light. For example, if the light source shown in (a) in FIG. 10 is used, both the light source 1 and the light source 5 emit light with the wavelength a. The light source 1 and the light source 5 may be controlled to alternately emit light at a frequency of emitting light for 1 millisecond (ms) each time, and the human eye light spot image is obtained at a frequency of once every 0.5 ms. Therefore, the obtained X human eye light spot images include a human eye light spot image obtained when the light source 1 emits light separately, and further include a human eye light spot image obtained when the light source 5 emits light separately. With reference to the X human eye light spot images and the light sources that emit light when the human eye light spot images are obtained, based on the type of light that can be filtered in the sub-region corresponding to the bright sub-region in the light spot in the light filtering unit, a light source can be matched with a light spot more accurately with reference to some or all of information including the type of light emitted by each light source, the relative position between the light spots in the human eye light spot image, the relative position between the light sources, and the like.

The foregoing uses the VR scenario as an example to describe an example of a process in which the VR head mounted display device 100 including the eye tracking module 412 performs eye tracking.

For ease of description, in some embodiments of this disclosure, the light source 4121 and the camera module 4122 that are in the eye tracking module 412 and that are configured to match a light source and a light spot are referred to as an eye tracking apparatus. The eye tracking apparatus may be applied to another electronic device in another scenario as an entire component, for example, may be applied to a mobile intelligent device, a large-screen display device, an intelligent in-vehicle device, or the like. This is not limited herein.

It may be understood that, a quantity and an arrangement manner of the light sources 4121 in the eye tracking apparatus shown in FIG. 10, and an arrangement manner of the light filtering units 1022 and the sub-regions 1023 in the light filtering component 1021 in the image sensor 1020 of the camera module 4122 are merely examples.

In some embodiments, the eye tracking apparatus includes M light sources 4121 and the camera module 4122, where M is a positive integer greater than or equal to 2, and one light source emits one type of light. The M light sources emit N different types of light to an eye of a user, where N is a positive integer greater than or equal to 2. In other words, the M light sources can emit two or more types of light, and different light sources may emit light of a same type.

The camera module 4122 includes the light filtering component 1021 and the image sensor 1020. The light filtering component 1021 is configured to filter at least a part of light reflected after the M light sources 4121 irradiate an eye. The light filtering component 1021 includes a plurality of light filtering units 1022, and the light filtering unit 1022 includes at least N sub-regions 1023. The light filtering unit 1022 filters at least the N different types of light, and one sub-region 1023 filters one type of light. The image sensor 1020 is configured to obtain the at least a part of filtered light to obtain the human eye light spot image. The light filtering component 1021 may include a sub-region that can filter the N types of light emitted by the M light sources, and may further include sub-regions that can filter more types of light.

After light of the light source is reflected by a human eye and before the reflected light is obtained by the image sensor 1020, the light filtering component 1021 filters the reflected light. Because each light source emits light of a corresponding type (for example, a wavelength or modulation), and each sub-region may transmit light of a corresponding type, when light of a light source reaches the light filtering component, if the light of the light source matches a sub-region, the light of the light source may pass through the sub-region, and a light spot is formed in the image sensor 1020. Therefore, one or more types of light that form the light spot in the human eye light spot image can be reflected by the light spot, which helps improve accuracy and efficiency of matching a light spot with a light source, and improves accuracy of a human eye fixation point determined by eye tracking.

In some embodiments, to prevent light emitted by the light source 4121 from affecting the human eye, the M light sources 4121 may be invisible light sources. The invisible light source may include a near-infrared light source, and/or a far-infrared light source, and/or an ultraviolet light source. For example, the plurality of invisible light sources 4121 may be infrared light sources, or may be ultraviolet light sources, or one part of the plurality of invisible light sources 4121 are infrared light sources, and the other part are ultraviolet light sources. This is not limited herein. When the invisible light sources 4121 are the infrared light sources, the invisible light sources 4121 may be near-infrared light sources, or may be far-infrared light sources, or one part of the invisible light sources 4121 are near-infrared light sources, and the other part are far-infrared light sources. This may be specifically selected based on an actual application requirement, and is not limited herein.

In some embodiments, one light source emits one type of light, one type of light is light with one wavelength, and different types of light have different wavelengths. For example, a wavelength of one type of light is 800 nanometers (nm), and a wavelength of another type of light may be 900 nm.

In some embodiments, one type of light is continuous light in one wavelength range or light in more than two (including two) discontinuous wavelength ranges, and wavelength ranges of different types of light do not include light with a same wavelength. For example, a wavelength of one type of light is 800 nm to 850 nm, and a wavelength of another type of light may be 900 nm to 950 nm. For another example, a wavelength of one type of light is 800 nm to 830 nm and 850 nm to 880 nm, and a wavelength of another type of light may be 900 nm to 930 nm and 950 nm to 980 nm. This is not limited herein.

In some embodiments, only a part of light in a type of light can pass through a sub-region that filters the type of light. For example, if a wavelength of a type of light is 800 nm to 850 nm, a sub-region that filters the type of light may filter only light with a wavelength of 820 nm, and light with another wavelength cannot pass through the sub-region. For another example, if a wavelength of a type of light is 800 nm to 850 nm, a sub-region that filters the type of light can filter only light with a wavelength of 820 nm to 830 nm, and light with another wavelength cannot pass through the sub-region. This is not limited herein.

In some embodiments, all light in a type of light can pass through a sub-region that filters the type of light. For example, if a wavelength of a type of light is 800 nm to 850 nm, a sub-region that filters the type of light can filter the light with a wavelength of 800 nm to 850 nm, and light with another wavelength cannot pass through the sub-region.

It may be understood that there may be a plurality of different manners for a specific quantity, wavelength distribution, and arrangement of the light sources 4121 in the eye tracking apparatus. The camera module 4122 may be placed at a plurality of different positions relative to the light source 4121. There may alternatively be a plurality of camera modules 4122. Likewise, there may alternatively be a plurality of manners for arranging the sub-regions in the light filtering unit in the light filtering component.

The following uses an example in which one type of light is light with one wavelength, and separately describes various possible manners of the light by using examples.

(1) The following first uses an example to describe the quantity, wavelength distribution, and the arrangement manner of the light sources 4121 in the eye tracking apparatus.

One light source emits light with one wavelength. Because the M light sources include light sources that can emit light of at least two different wavelengths, a quantity of the M light sources is at least 2.

It may be understood that the quantity of the M light sources may be 3, 4, 5, 6, 7, 8, 9, 10, or more. This is not limited herein. When there are more light sources, light of more different angles can be more comprehensively irradiated to a human eye, so that there are more light spots in the human eye light spot image, and a finally calculated fixation point of the human eye is more accurate. However, a larger quantity of light sources results in higher energy consumption. Therefore, an electronic device to which the eye tracking apparatus is applied selects an appropriate quantity of light sources based on an actual application requirement.

For ease of understanding, the following describes the wavelength distribution of the M light sources by using an example in which the quantity of the M light sources is 8.

The M light sources include light sources with at least two wavelengths.

In some embodiments, a wavelength of light emitted by each light source is different from that of light emitted by another light source. That is, the eight light sources include light sources that can emit light with eight different wavelengths. Because the wavelengths of the light emitted by the light sources are different, a light source that emits the light of the wavelength may be determined directly based on the wavelength of the light that forms a light spot in the human eye light spot image, and the light source can be accurately, quickly, and ambiguously matched with the light spot, thereby improving accuracy of determining a human eye fixation point by eye tracking.

However, if there are too many wavelengths of light emitted by the light sources, more sub-regions in the light filtering unit are used for filtering the light with these wavelengths. As a result, an area of the light filtering unit is too large, and most light cannot pass through the light filtering component, which is not conducive to obtaining a complete light spot. Therefore, in some embodiments, the plurality of invisible light sources include at least two light sources that emit light of a same wavelength. A quantity of different types of sub-regions is reduced, and the area of the light filtering unit is correspondingly reduced, so that a more accurate shape and size of a light spot formed by irradiation and reflection can be obtained, thereby improving accuracy of determining a human eye fixation point by eye tracking.

For example, light sources that emit light with a same wavelength are referred to as a group of light sources. A larger quantity of groups of sources indicates that a matching relationship between a light spot and a light source can be determined more quickly, and a smaller quantity of groups of light sources indicates that a complete light spot can be obtained more quickly.

In some embodiments, the eight light sources (the light source 1, the light source 2, the light source 3, the light source 4, the light source 5, the light source 6, the light source 7, and the light source 8) can emit light with seven different wavelengths (the wavelength a, the wavelength b, the wavelength c, the wavelength d, a wavelength e, a wavelength f, and a wavelength g), that is, there are seven groups of light sources. One group of light sources includes two light sources (for example, both the light source 8 and the light source 1 can emit light with the wavelength a).

In some embodiments, the eight light sources (the light source 1, the light source 2, the light source 3, the light source 4, the light source 5, the light source 6, the light source 7, and the light source 8) can emit light with six different wavelengths (the wavelength a, the wavelength b, the wavelength c, the wavelength d, a wavelength e, and a wavelength f), that is, there are six groups of light sources. There may be one group of light sources including three light sources (for example, the light source 7, the light source 8, and the light source 1 may all emit light with the wavelength a), or there may be two groups of light sources each including two light sources (for example, the light source 8 and the light source 1 may both emit light with the wavelength a, and the light source 7 and the light source 2 may both emit light with the wavelength b).

In some embodiments, the eight light sources (the light source 1, the light source 2, the light source 3, the light source 4, the light source 5, the light source 6, the light source 7, and the light source 8) can emit light with five different wavelengths (the wavelength a, the wavelength b, the wavelength c, the wavelength d, and a wavelength e), that is, there are five groups of light sources. There may be one group of light sources including four light sources (for example, the light source 6, the light source 7, the light source 8, and the light source 1 may all emit light with the wavelength a), or there may be one group of light sources including three light sources and another group of light sources including two light sources (for example, the light source 7, the light source 8, and the light source 1 may all emit light with the wavelength a, and the light source 6 and the light source 2 both emit light with the wavelength b). Alternatively, there may be three groups of light sources each including two light sources (for example, both the light source 8 and the light source 1 may emit light with the wavelength a, both the light source 7 and the light source 2 emit light with the wavelength b, and both the light source 6 and the light source 3 emit light with the wavelength c).

In some embodiments, the eight light sources can emit four types of light with different wavelengths, three types of light with different wavelengths, two types of light with different wavelengths, or the like. This is not limited herein.

The eight light sources may be arranged in different manners.

In some embodiments, the eight light sources are evenly arranged on a first surface (for example, an end surface that is of the lens tube and that is close to a human eye in FIG. 2A) in a centrosymmetric regular shape. Evenly arrangement in a centrosymmetric regular shape can avoid a dead angle of irradiating a human eye, ensure that there are light sources that can irradiate the human eye at all angles, and reduce a probability of an ambiguous light source, thereby improving accuracy of determining a human eye fixation point by eye tracking.

Figure 12:
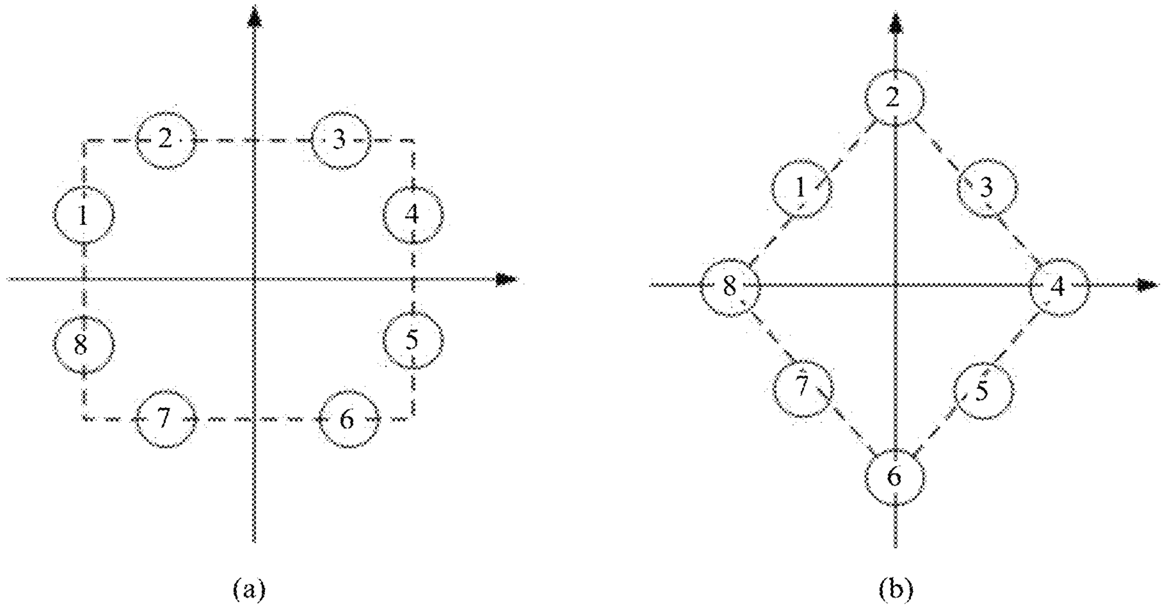
FIG. 12 is a schematic diagram of an example of eight light sources arranged in several regular shapes according to an embodiment of this disclosure.

For example, (a) in FIG. 10 shows an example in which the eight light sources are evenly arranged in a circle. For example, (a) in FIG. 12 shows an example in which the eight light sources are evenly arranged in a rectangle. For example, (b) in FIG. 12 shows an example in which the eight light sources are evenly arranged in a rhombus.

It may be understood that, in some other embodiments, the eight light sources are evenly arranged in another centrosymmetric regular pattern. This is not limited herein.

In some embodiments, the eight light sources are arranged in an irregular shape on the first surface. Arrangement in an irregular shape can make light that is irradiated by the light source to the human eye and then reflected to the camera module have various different changes, to obtain light spots at various different positions in the human eye, so that a motion status of the human eye can be more accurately determined, thereby improving accuracy of determining a human eye fixation point by eye tracking.

Figure 13:
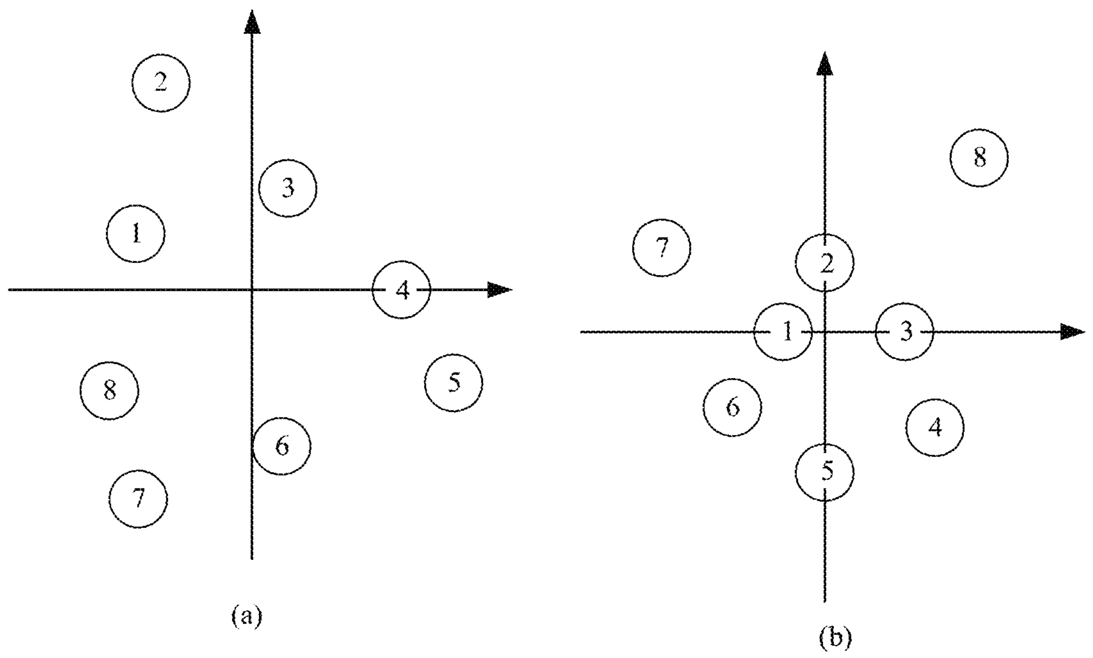
FIG. 13 is a schematic diagram of an example of eight light sources arranged in several irregular shapes according to an embodiment of this disclosure.

For example, (a) in FIG. 13 shows an example in which the eight invisible light sources are arranged in an irregular shape. For example, (b) in FIG. 13 shows an example in which the eight invisible light sources are arranged in another irregular shape.

In some embodiments, a center of the arrangement shape of the M light sources is located on a same horizontal line as a center of an eyeball of a human eye during using of the eye tracking apparatus.

It may be understood that a spacing between the light sources in the M light sources may be set based on the arrangement manner of the light sources and a distance between the invisible light source and the eyeball during using of the eye tracking apparatus. This is not limited herein.

In some embodiments, when there are a plurality of light sources that can emit light with a same wavelength, the light sources that emit light with the same wavelength are not adjacent. In some embodiments, a spacing between the plurality of light sources that can emit light with the same wavelength is greater than a minimum spacing between light sources that can emit light with different wavelengths. For example, as shown in (a) in FIG. 10, a spacing between the light source 1 and the light source 5 that can emit light with the same wavelength a is greater than a spacing between the light source 8 that can emit light with the wavelength d and the light source 7 that can emit light with the wavelength c. In this way, a probability of ambiguity generated during a light spot is matched with a light source can be reduced, and accuracy of determining a human eye fixation point by eye tracking is improved.

The following uses an example in which the eight light sources are arranged on one surface in a circular shape, to describe examples of several light source arrangement structures in the eye tracking apparatus with reference to several wavelength distribution manners.

Figure 14:
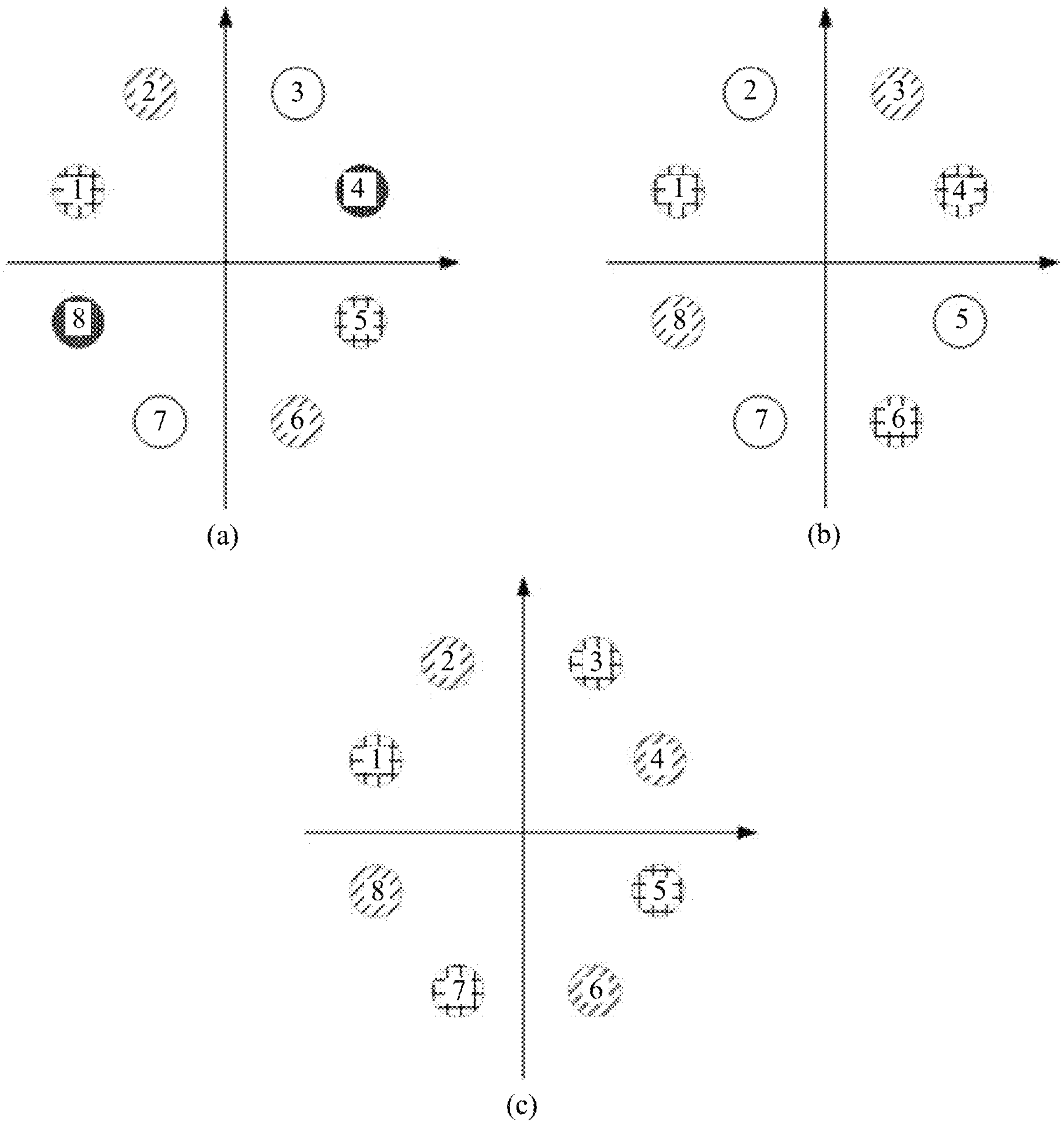
FIG. 14 is a schematic diagram of several examples of arrangement structures of eight light sources according to an embodiment of this disclosure.

For example, as shown in (a) in FIG. 14, the eight invisible light sources may be divided into four groups: the light source 1 and the light source 5, the light source 2 and the light source 6, the light source 3 and the light source 7, and the light source 4 and the light source 8. Two light sources in each group emit light with a same wavelength, and any two of the four groups of light sources emit light with different wavelengths.

For example, as shown in (b) in FIG. 14, the eight invisible light sources may be divided into three groups: the light source 1, the light source 4, and the light source 6, the light source 2, the light source 5, and the light source 7, and the light source 3 and the light source 8. Light sources in each group emit light with a same wavelength, and any two of the three groups of light sources emit light with different wavelengths.

For example, as shown in (c) in FIG. 14, the eight invisible light sources may be divided into two groups: the light source 1, the light source 3, the light source 5, and the light source 7, and the light source 2, the light source 4, the light source 6, and the light source 8. Light sources in each group emit light with a same wavelength, and the two groups emit light with different wavelengths.

(2) The following uses an example to describe a quantity and an arrangement manner of the camera modules 4122 in the eye tracking apparatus.

The quantity of the camera modules 4122 is at least 1.

In some embodiments, the quantity of the camera modules 4122 may be 2, 3, 4, 5, or more. This is not limited herein. A larger quantity of camera modules 4122 indicates that a light source can be more accurately matched with a light spot, but this causes greater power consumption. Therefore, a proper quantity of camera modules is selected based on an actual application requirement.

The camera module 4122 may be located in a position at which light reflected after light emitted by the M light sources 4121 is irradiated to an eyeball can be obtained. Specifically, a position of the camera module 4122 may be determined based on the quantity and the arrangement manner of the light sources, a position of an eyeball of a human eye when the eye tracking apparatus is used, and the like. This is not limited herein.

In some embodiments, the camera module 4122 and the M light sources 4121 may be located on a same surface, for example, the end surface in FIG. 2A that is of the lens tube and that is close to the human eye.

In some embodiments, the camera module 4122 may be located in a position outside a geometric shape including the M light sources. In this way, light of the display can enter the human eye through the lens without being blocked.

Figure 15:
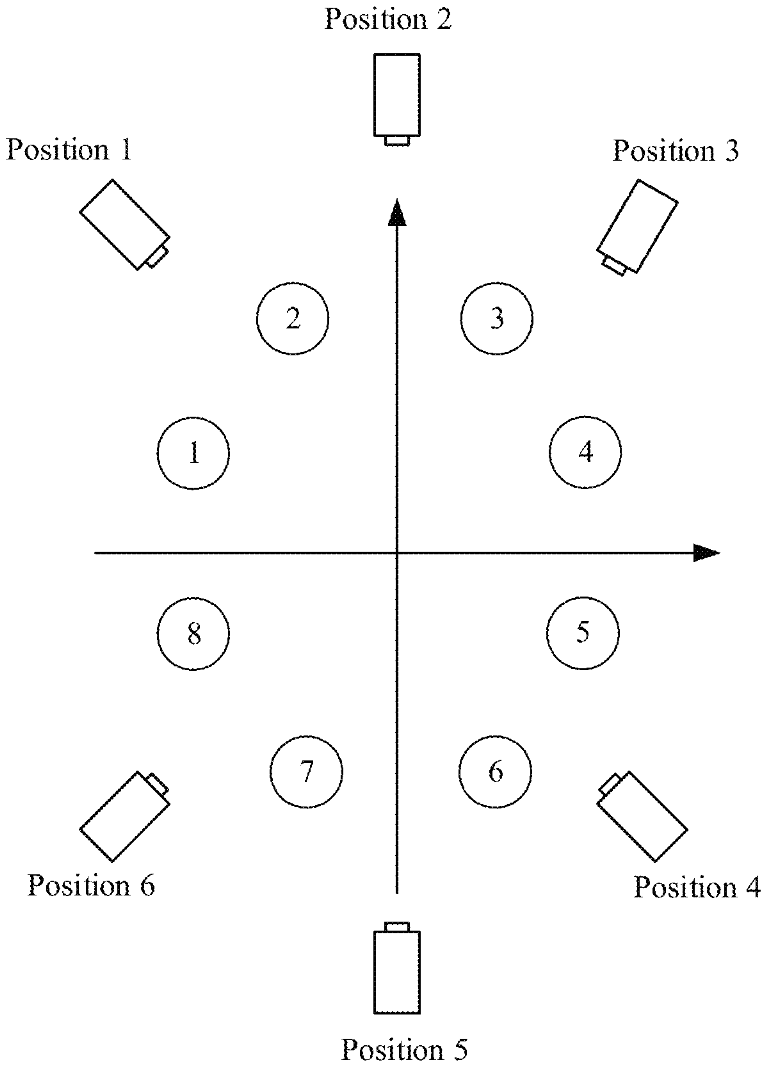
FIG. 15 is a schematic diagram of an example of a disposition position of a camera module according to an embodiment of this disclosure.

For example, the eight light sources in the eye tracking apparatus are evenly distributed in a circular shape, and there is only one camera module. As shown in FIG. 15, the camera module may be disposed at any one of a position 1, a position 2, a position 3, a position 4, a position 5, and a position 6 shown in the figure.

In some embodiments, to obtain more comprehensive light reflected after light emitted by a light source is irradiated to a human eye, the camera module 4122 may alternatively be located in a position in the geometric shape including the M light sources, or may be located on a different surface from the M light sources 4121, thereby improving accuracy of determining a human eye fixation point by eye tracking. This is not limited herein.

(3) The following uses an example to describe an arrangement manner of sub-regions in the light filtering unit 1022 of the camera module 4122.

It may be understood that, if the light source in the eye tracking apparatus may emit light with N different wavelengths, one light filtering unit includes N sub-regions that can filter light with different wavelengths, and may further include a sub-region that can filter light with another wavelength.

In a light filtering unit, each type of sub-region may include only one or more sub-regions. This is not limited herein.

The sub-regions may be arranged in the light filtering unit in many manners. For example, sub-regions that filter light with different wavelengths may be arranged based on a wavelength size, or may be arranged randomly. This is not limited herein.

The sub-region in the light filtering unit may be of various different shapes, and may be specifically determined based on a shape of a pixel in the image sensor. Sub-regions of different shapes may correspond to shapes of different pixels in the sensor, so that the sensor can obtain more comprehensive and accurate light filtered by the light filtering component, thereby improving accuracy of matching a light spot with a light source, and improving accuracy of determining a human eye fixation point by eye tracking. The sub-region 1023 in the light filtering unit 1022 in FIG. 10 is shown in a square shape.

Quantities of the sub-regions that filter light with different wavelengths in the light filtering unit may be the same or may be different. This is not limited herein. Sizes of the sub-regions that filter light with different wavelengths in the light filtering unit may be the same or may be different. This is not limited herein. Shapes of the sub-regions that filter light with different wavelengths in the light filtering unit may be the same or may be different. This is not limited herein.

Specifically, a quantity, a size, and a shape of the sub-region that filters light with each wavelength in the light filtering unit may be set based on an actual application requirement. This is not limited herein.

In some embodiments, an area of each sub-region is greater than or equal to one pixel of the image sensor and/or less than or equal to five pixels of the image sensor, so that whether there is corresponding light passing through each sub-region can be conveniently obtained and represented by the image sensor. In some embodiments, the area of each sub-region is less than 1/N of an area of a light spot in the human eye light spot image, where N may be a quantity of types of light emitted by the light sources. For example, the light sources shown in (a) in FIG. 10 can emit light with four wavelengths. Therefore, the area of each sub-region may be less than ¼ of the area of one light spot in the human eye light spot image. If the area of one light spot in the human eye light spot image is less than 16 pixels, the area of each sub-region may be less than two pixels. In this way, each light spot is covered by at least four sub-regions, which can ensure that more wavelength information is obtained by using each light spot, thereby improving accuracy of determining a human eye fixation point by eye tracking.

For example, the sub-region is a square. As shown in (b) in FIG. 10, four square sub-regions 1023 are arranged into a larger square, which is used as the light filtering unit 1022. The plurality of light filtering units 1022 form a larger light filtering components 1021 that can cover the image sensor 1020.

In conclusion, the foregoing embodiments are merely intended for describing the technical solutions of this disclosure, but not for limiting this disclosure. Although this disclosure is described in detail with reference to the foregoing embodiments, persons of ordinary skill in the art should understand that they may still make modifications to the technical solutions described in the foregoing embodiments or make equivalent replacements to some technical features thereof, without departing from the scope of the technical solutions of embodiments of this disclosure.

Although this disclosure is described with reference to some embodiments, it does not mean that a characteristic of this disclosure is limited only to this implementation. On the contrary, a purpose of describing this disclosure with reference to an implementation is to cover another option or modification that may be derived based on the claims of this disclosure. To provide an in-depth understanding of this disclosure, the following descriptions include a plurality of specific details. This disclosure may be alternatively implemented without using these details. In addition, to avoid confusion or blurring a focus of this disclosure, some specific details are omitted from the description. It should be noted that embodiments in this disclosure and the features in embodiments may be mutually combined in the case of no conflict.

According to the context, the term "when" used in the foregoing embodiments may be interpreted as "if", "after", "in response to determining", or "in response to detecting". Similarly, according to the context, the phrase "when it is determined that" or "if (a stated condition or event) is detected" may be interpreted as a meaning of "if it is determined that", "in response to determining", "when (a stated condition or event) is detected", or "in response to detecting (a stated condition or event)".

In descriptions of embodiments of this disclosure, it should be noted that, unless otherwise specified and limited, terms "installation" and "connection" shall be understood in a broad sense. For example, "connection" may be a detachable connection, or may be a non-detachable connection, and may be a direct connection, or may be an indirect connection by using an intermediate medium. Orientation terms mentioned in embodiments of this disclosure, for example, "on", "below", "left", "right", "inside", "outside", are merely directions based on the accompanying drawings. Therefore, the orientation terms are used to better and more clearly describe and understand embodiments of this disclosure, instead of indicating or implying that a specified apparatus or element has a specific orientation, and be constructed and operated in the specific orientation. Therefore, this cannot be understood as a limitation on embodiments of this disclosure. In addition, "a plurality of" means at least two.

Reference to "an embodiment", "some embodiments", or the like described in this specification indicates that one or more embodiments of this disclosure include a specific feature, structure, or characteristic described with reference to the embodiment. Therefore, statements such as "in an embodiment", "in some embodiments", "in some other embodiments", and "in other embodiments" that appear at different places in this specification do not necessarily mean referring to a same embodiment. Instead, the statements mean "one or more but not all of embodiments", unless otherwise specifically emphasized in another manner. The terms "include", "have", and their variants all mean "include but are not limited to", unless otherwise specifically emphasized in another manner. All or some of the foregoing embodiments may be implemented by using software, hardware, firmware, or any combination thereof. When software is used to implement the embodiments, all or a part of the embodiments may be implemented in a form of a computer program product. The computer program product includes one or more computer instructions. When the computer program instructions are loaded and executed on the computer, the procedure or functions according to embodiments of this disclosure are all or partially generated. The computer may be a general-purpose computer, a dedicated computer, a computer network, or another programmable apparatus. The computer instructions may be stored in a computer-readable storage medium, or may be transmitted from a computer-readable storage medium to another computer-readable storage medium. For example, the computer instructions may be transmitted from a website, computer, server, or data center to another website, computer, server, or data center in a wired (for example, a coaxial cable, an optical fiber, or a digital subscriber line) or wireless (for example, infrared, radio, or microwave) manner. The computer-readable storage medium may be any usable medium accessible by the computer, or a data storage device, for example, a server or a data center, integrating one or more usable media. The usable medium may be a magnetic medium (for example, a floppy disk, a hard disk, or a magnetic tape), an optical medium (for example, a digital versatile disc (DVD)), a semiconductor medium (for example, a solid-state drive), or the like.

Persons of ordinary skill in the art may understand that all or some of the processes of the methods in embodiments may be implemented by a computer program instructing related hardware. The program may be stored in a computer-readable storage medium. When the program runs, the processes of the methods in embodiments are performed. The foregoing storage medium includes any medium that can store program code, for example, a read-only memory (ROM), a random access memory (RAM), a magnetic disk, or an optical disc.

What is claimed is:

1. An apparatus, comprising:

M light sources configured to emit N different types of light, wherein M is a first positive integer greater than or equal to 2, and wherein N is a second positive integer greater than or equal to 2; and a camera comprising:

a light filtering component comprising a plurality of light filtering units, each light filtering unit comprising at least N different types of sub-regions, wherein the N different types of sub-regions are configured to filter different types of light, and wherein the light filtering component is configured to filter reflected light that is reflected after the M light sources irradiate an eye; and an image sensor configured to obtain the reflected light to obtain an eye light spot image, wherein the reflected light forms at least one light spot on the eye light spot image, and wherein N is less than M, wherein at least two light sources of the M light sources are configured to emit light of a same type, and wherein the at least two light sources that emit light of that same type are not adjacent to each other in the apparatus.

2. The apparatus of claim 1, wherein the image sensor comprises an array of pixels, wherein each light spot comprises a plurality of pixels, and wherein each light spot corresponds to a sub-region of the N different types of sub-regions.

3. The apparatus of claim 2, wherein an area of a first sub-region of the sub-regions is less than or equal to five pixels.

4. The apparatus of claim 2, wherein a first area of a first sub-region of the sub-regions is less than or equal to 1/N of a second area of one light spot.

5. The apparatus of claim 4, wherein the sub-regions are in a one-to-one correspondence with the pixels.

6. The apparatus of claim 5, wherein a quantity of light spots on the eye light spot image is less than M.

7. The apparatus of claim 6, wherein the apparatus further comprises one or more processors configured to:

obtain an eye position of the eye; and receive the eye light spot image from the camera.

8. The apparatus of claim 7, wherein M is greater than or equal to 4, or wherein N is greater than or equal to 4.

9. The apparatus of claim 8, wherein the M light sources comprise a plurality of light source groups, wherein each light source group comprises at least two light sources that emit light of the same type, and wherein light sources in different light source groups emit light of different types.

10. The apparatus of claim 9, wherein light sources in each light source group emit light at different frequencies.

11. A method, comprising:

emitting N different types of light from M light sources, wherein Mis a first positive integer greater than or equal to 2, and wherein N is a second positive integer greater than or equal to 2;

filtering, by a light filtering component, reflected light that is reflected after the M light sources irradiate an eye, wherein the light filtering component comprises a plurality of light filtering units, wherein each light filtering unit comprises at least N different types of sub-regions, and wherein the different types of sub-regions filter different types of reflected light; and obtaining, by an image sensor, the reflected light to obtain an eye light spot image, wherein the reflected light forms at least one light spot on the eye light spot image, and wherein N is less than M, wherein at least two light sources of the M light sources emit light of a same type, and wherein the at least two light sources that emit light of that same type are not adjacent to each other in an apparatus performing the method.

12. The method of claim 11, wherein there is a correspondence between a first sub-region of the sub-regions and a pixel of the image sensor, wherein each light spot comprises a plurality of pixels, and wherein one light spot corresponds to a sub-region of the N different types of sub-regions.

13. The method of claim 12, wherein a first area of the first sub-region is less than or equal to five pixels.

14. The method of claim 13, wherein the first area of the first sub-region is less than or equal to 1/N of a second area of one light spot.

15. The method of claim 14, wherein the sub-regions are in a one-to-one correspondence with the pixels.

16. The method of claim 15, further comprising obtaining a fixation point of the eye.

17. The method of claim 16, wherein a quantity of light spots on the eye light spot image is less than M.

18. The method of claim 17, wherein the reflected light forms a first light spot on the eye light spot image, wherein the first light spot is formed by reflected light corresponding to a single one of the N different types of light such that the first light spot is formed by light passing through only sub-regions of that single one type of sub-region, and wherein the first area of the first sub-region is less than or equal to 1/N of the second area of the first light spot.

19. The method of claim 18, wherein the M light sources comprise a plurality of light source groups, wherein each light source group comprises at least two light sources that emit light of the same type, and wherein light sources in different light source groups emit light of different types.

20. A computer program product comprising computer-executable instructions that are stored on a non-transitory computer-readable medium and that, when executed by at least one processor, cause an apparatus to:

emit N different types of light from M light sources, wherein M is a first positive integer greater than or equal to 2, and wherein N is a second positive integer greater than or equal to 2;

filter, by a light filtering component in a camera, reflected light that is reflected after the M light sources irradiate an eye, wherein the light filtering component comprises a plurality of light filtering units, wherein each light filtering unit comprises at least N different types of sub-regions, and wherein the different types of sub-regions filter different types of reflected light; and obtain, by an image sensor in the camera, the reflected light to obtain an eye light spot image, wherein the reflected light forms at least one light spot on the eye light spot image, and wherein N is less than M, wherein at least two light sources of the M light sources are configured to emit light of a same type, and wherein the at least two light sources that emit light of that same type are not adjacent to each other in the apparatus.

* * * * *